US008247573B2

(12) United States Patent
Kühnert et al.

(10) Patent No.: US 8,247,573 B2
(45) Date of Patent: *Aug. 21, 2012

(54) SUBSTITUTED N-(2-MERCAPTOPYRIDIN-3-YL)AMIDES AS KCNQ2/3 MODULATORS

(75) Inventors: Sven Kühnert, Düren (DE); Beatrix Merla, Aachen (DE); Achim Kless, Aachen (DE); Gregor Bahrenberg, Monschau-Konzen (DE); Wolfgang Schröder, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/720,836

(22) Filed: Mar. 10, 2010

(65) Prior Publication Data
US 2010/0234428 A1 Sep. 16, 2010

Related U.S. Application Data

(60) Provisional application No. 61/159,563, filed on Mar. 12, 2009.

(30) Foreign Application Priority Data

Mar. 12, 2009 (EP) .................................. 09003604

(51) Int. Cl.
*C07D 213/72* (2006.01)
*A61K 31/44* (2006.01)
(52) U.S. Cl. ........................................ 546/297; 514/349
(58) Field of Classification Search ........................ None
See application file for complete search history.

(56) References Cited

U.S. PATENT DOCUMENTS

| | | | |
|---|---|---|---|
| 2002/0128277 A1 | 9/2002 | Dworetzky et al. | |
| 2010/0234372 A1 | 9/2010 | Kuhnert et al. | |
| 2010/0234419 A1 | 9/2010 | Kuhnert et al. | |
| 2010/0234421 A1 | 9/2010 | Kuhnert et al. | |
| 2010/0234429 A1 | 9/2010 | Kuhnert et al. | |

FOREIGN PATENT DOCUMENTS

| | | |
|---|---|---|
| DE | 27 06977 A1 | 2/1978 |
| EP | 0 480 258 A2 | 4/1992 |
| EP | 0 716 077 A1 | 12/1996 |
| EP | 0 900 824 A1 | 10/1999 |
| EP | 1 449 841 A1 | 8/2004 |
| FR | 2 532 939 | 11/1984 |
| WO | 96 26925 A1 | 9/1996 |
| WO | 00 42026 | 7/2000 |
| WO | 01 10380 A2 | 2/2001 |
| WO | 01 10381 A2 | 2/2001 |
| WO | 02 066036 A1 | 9/2002 |
| WO | 02 074388 A1 | 9/2002 |
| WO | 02 081728 | 10/2002 |
| WO | 2004 026816 A1 | 4/2004 |
| WO | 2004 058704 A2 | 7/2004 |
| WO | 2004 058704 A3 | 7/2004 |
| WO | 2005 035514 A2 | 4/2005 |
| WO | 2005 105733 | 11/2005 |
| WO | 2006 051311 A1 | 5/2006 |
| WO | 2006 092143 A1 | 9/2006 |
| WO | 2006 122799 A1 | 11/2006 |
| WO | 2006 122800 A | 11/2006 |
| WO | 2007 015767 A | 2/2007 |
| WO | 2007 030582 A2 | 3/2007 |
| WO | 2007 057447 A | 5/2007 |
| WO | 2008-011080 A2 | 1/2008 |
| WO | 2008 011110 A2 | 1/2008 |
| WO | 2008 012532 A2 | 1/2008 |
| WO | 2008 046582 A1 | 4/2008 |
| WO | 2009 018466 A1 | 2/2009 |
| WO | 2009 019149 A1 | 2/2009 |
| WO | 2009-052078 A1 | 4/2009 |

OTHER PUBLICATIONS

CAPLUS 1972:59403.*
Bennett et al; "A peripheral monoeuropathy in rat that produces disorders of pain sensation like those seen in man" Pain, 33 (1988) 87-107.
Gordon Blackburn-Munro; "The anticonvulsant retigabine attenuates nociceptive behaviours in rat models of persistent and neuropathic pain"; European Journal of Pharmacology 460 (2003) 109-116.
De Sarro et al; "Influence of retigabine on the anticonvulsant activity of some antiepileptic drugs against audiogenic seizures in DBA/2 mice"; Naunyn-Schmiedeberg's Arch Pharmacol (2001) 363: 330-336.
Dencker; "Effect of the new antiepileptic drug retigabine in a rodent model of mania"; ScienceDirect, Epilepsy & Behavior 12 (2008) 49-53.
Dost et al; "The anti-hyperalgesic activity of retigabine is mediated by KCNQ potassium channel activation"; Naunyn-Schmiedeberg's Arch Pharmacol (2004) 369 : 382-390.
Dubuisson et al; "The formalin test: A quantitative study of the analgesic effects of morphine, meperidine, and brain stem stimulation in rats and cats"Pain, 4 (1977) 161-174.
Gribkoff; "The therapeutic potential of neuronal Kv7 (KCNQ) channel modulators: an update"; Expert Opin. Ther. Targets (2008) 12(5): 565-581.
Gribkoff; "The therapeutic potential of neuronal KCNQ channel modulators" Expert Opin. Ther. Targets (2003) 7(6): 737-748.
Hansen et al: "The neuronal KCNQ channel opener retigabine inhibits locomotor activity and reduces forebrain excitatory responses to the psychostimulants cocaine, methylphenidate and phencyclidine"; ScienceDirect, European Journal of Pharmacology 570 (2007) 77-88.
Kim, et al; "An experimental model for peripheral neuropathy produced by segmental spinal nerve ligationin the rat"; Pain, 50 (1992) 355-363.
Korsgaard,et al; "Anxiolytic Effects of Maxipost (BMS-204352) and Retigabine via Activation of Neuronal Kv7 Channels"; The Journal of Pharmacology and Experimental Therapeutics vol. 314, No. 1 :282-292, 2005.

(Continued)

*Primary Examiner* — Janet Andres
*Assistant Examiner* — Heidi Reese
(74) *Attorney, Agent, or Firm* — Norris McLaughlin & Marcus, P.A.

(57) ABSTRACT

The invention relates to substituted N-(2-mercaptopyridin-3-yl)amides, methods for the preparation thereof, medicaments containing these compounds and the use of these compounds for the preparation of medicaments.

14 Claims, No Drawings

OTHER PUBLICATIONS

Litchfield, Jr. et al; "A simplified method of evaluating dose-effect experiments"; Stamford Research Laboratories, American Cyanamid Company, Stamford, Connecticut, Royal Society of Medicine 1948; pp. 99-113.

Micel, et al; "Molecular pharmacology and therapeutic potential of neuronal Kv7-modulating drugs"; ScienceDirect, Current Opinion in Pharmacology 2008, 8:65-74.

Nielsen*, et al; "Pharmacological characterisation of acid-induced muscle allodynia in rats"; ScienceDirect, European Journal of Pharmacology 487 (2004) 93-103.

Passmore, et al; "KCNQ/M Currents in Sensory Neurons: Significance for Pain Therapy"; The Journal of Neuroscience, Aug. 6, 2003 • 23(18):7227-7236 • 7227.

Richte, et al; "Antidystonic effects of Kv7 (KCNQ) channel openers in the dtsz mutant, an animal model of primary paroxysmal dystonia"; British Journal of Pharmacology (2006) 149, 747-753.

Streng, et al; "Urodynamic effects of the K+ channel (KCNQ) opener retigabine in freely moving, conscious rats"; The Journal of Urology, vol. 172, 2054-2058, Nov. 2004.

Wickenden et al; "KCNQ potassium channels: drug targets for the treatment of epilepsy and pain"; Expert Opinion, Ther. Patents (2004) 14(4): 457-469.

F. A. Carey, R. J. Sundberg, Advanced Organic Chemistry, Parts A and B, Springer, 5th edition, 2007, Table of Contents of Part A only.

D'Amour and Smith (J. Pharm. Exp. Ther. 72, 74 79 (1941).

J. March, Advanced Organic Chemistry, Wiley & Sons, 6th edition, 2007, Table of Contents only.

Dorwald, F. Zargaoza, Side reactions in Organic Synthesis, A guide to sucsessful synthesis design; Wiley-VCH, Weinheim, Preface, p. IS (2005).

Hewawasam, Piyasena et al, The synthesis and structure-activity relationships of 3-amino-4-benzylquinolin-2-ones: discovery of novel KCNQ2 channel openers; Biorganic & Medicinal Chemistry Letters 14 (2004) 1615-1618.

Martin, Yvonne C., et al, Do Structurally similar molecules have similar biological activity?; J. Med. Chem. 2002, 45, 4350-4358.

Patani, G. et al, Bioisosterism: a ratiional approach in drug design, Chem. Rev. 1996, pp. 3147-3176.

Silverman, R. The organic chemistry of drug design and drug action, 2004, Elsevier, 2nd edition, p. 9.

Wermuth C. G., "Molecular variations based on isosteric replacements", Practice of medicinal Chemistry, XX, XX, Jan. 1, 1996, pp. 203-237.

Yoo, Kwang Ho et al, "Beckmann rearrangement using indium (III) chloride: synthesis of substituted oxazoloquinolines from the corresponding ketoximes of 3-acyl-1H-quinolin-4-ones", Synthesis 2006, No. 10, Apr. 27, 2006, pp. 1599-1612.

* cited by examiner

SUBSTITUTED N-(2-MERCAPTOPYRIDIN-3-YL)AMIDES AS KCNQ2/3 MODULATORS

This application is a non-provisional utility patent application claiming priority of U.S. Provisional Application No. 61/159,563 filed Mar. 12, 2009; and European Patent Application No. 09003604.7 filed Mar. 12, 2009.

The invention relates to substituted N-(2-mercaptopyridin-3-yl)amides, methods for the preparation thereof, medicaments containing these compounds and the use of these compounds for the preparation of medicaments.

The treatment of pain, in particular neuropathic pain, is of great importance in medicine. There is a worldwide need for effective pain therapies. The urgent need for action to find targeted, patient-appropriate treatment for chronic and non-chronic pain conditions, this being understood as the successful and satisfactory treatment of pain for the patient, is also documented in the large number of scientific works that have been published in recent times in the field of applied analgesics and basic research into nociception.

A pathophysiological feature of chronic pain is the over-excitability of neurons. Neuronal excitability is decisively influenced by the activity of $K^+$ channels, since these significantly determine the resting potential of the cell and hence the excitability threshold. Heteromeric $K^+$ channels of the molecular subtype KCNQ2/3 (Kv7.2/7.3) are expressed in neurons of various regions of the central (hippocampus, amygdala) and peripheral (dorsal root ganglia) nervous system and regulate the excitability thereof. Activation of KCNQ2/3 $K^+$ channels leads to a hyperpolarisation of the cell membrane and, accompanying this, to a decrease in the electrical excitability of these neurons. KCNQ2/3-expressing neurons of the dorsal root ganglia are involved in the transmission of nociceptive stimuli from the periphery into the spinal cord (Passmore et al., J. Neurosci. 2003; 23 (18):7227-36).

It has accordingly been possible to detect an analgesic activity in preclinical neuropathic and inflammatory pain models for the KCNQ2/3 agonist retigabine (Blackburn-Munro and Jensen, Eur J. Pharmacol. 2003; 460 (2-3):109-16; post et al., Naunyn Schmiedeberg's Arch Pharmacol 2004; 369 (4): 382-390).

The KCNQ2/3 $K^+$ channel thus represents a suitable starting point for the treatment of pain; in particular pain chosen from the group consisting of chronic pain, neuropathic pain, inflammatory pain and muscular pain (Nielsen et al., Eur J. Pharmacol. 2004; 487 (1-3): 93-103), in particular neuropathic and inflammatory pain.

Moreover, the KCNQ2/3 $K^+$ channel is a suitable target for therapy of a large number of further diseases, such as, for example, migraine (US2002/0128277), cognitive diseases (Gribkoff, Expert Opin Ther Targets 2003; 7 (6): 737-748), anxiety states (Korsgaard et al., J Pharmacol Exp Ther. 2005, 14 (1): 282-92), epilepsy (Wickenden et al., Expert Opin Ther Pat 2004; 14 (4): 457-469; Gribkoff, Expert Opin Ther Targets 2008, 12 (5): 565-81; Miceli et al., Curr Opin Pharmacol 2008, 8 (1): 65-74), urinary incontinence (Streng et al., J Urol 2004; 172: 2054-2058), dependency (Hansen et al., Eur J Pharmacol 2007, 570 (1-3): 77-88), mania/bipolar disorders (Dencker et al., Epilepsy Behav 2008, 12 (1): 49-53), dystonia-associated dyskinesias (Richter et al., Br J Pharmacol 2006, 149 (6): 747-53).

Substituted pyridine derivatives (WO 2006/092143), substituted heteroaryl compounds (WO 01/010380) and nitrogen-containing heteroaryl derivatives (WO 2006/051311) having an affinity for the KCNQ receptor are known from the prior art.

There is a need for further compounds having comparable or better properties, not only in regard to affinity for KCNQ2/3 as such (potency, efficacy).

For instance, it can be advantageous to improve the metabolic stability, the solubility in aqueous media or the permeability of the compounds. These factors can have a beneficial effect on oral bioavailability or can alter the PK/PD (pharmacokinetic/pharmacodynamic) profile, which can lead to a more favourable period of action, for example.

A weak or non-existent interaction with transporter molecules, which are involved in the uptake and excretion of medicaments, can also be taken as an indication of improved bioavailability and at most low medicament interaction. Furthermore, interactions with the enzymes involved in the breakdown and excretion of medicaments should also be as low as possible, since such test results likewise indicate that at most low or even no medicament interactions whatsoever are to be anticipated.

It can further be advantageous if the compounds exhibit a high selectivity towards other receptors of the KCNQ family (specificity), for example towards KCNQ1, KCNQ3/5 or KCNQ4. A high selectivity can have a favourable effect on the side-effects profile. It is known, for example, that compounds which (also) bind to KCNQ1 are associated with a high risk of cardiac side effects, for which reason a high selectivity towards KCNQ1 can be desirable. A high selectivity towards other receptors can also be advantageous, however. A low affinity for the hERG ion channel or for the L-type calcium ion channel (phenyl alkylamine, benzothiazepine, dihydropyridine binding sites) can be advantageous, as these receptors are associated with the occurrence of cardiac side effects. Overall an improved selectivity with regard to binding to other endogenous proteins (i.e. receptors or enzymes for example) can lead to an improvement in the side-effects profile and hence to an improved compatibility.

An object of the invention was therefore to provide novel compounds having advantages over the prior art compounds. The compounds should in particular be suitable as pharmacological active ingredients in medicaments, preferably in medicaments for the treatment of disorders or diseases which are at least partly mediated by KCNQ2/3 $K^+$ channels.

This object is achieved by the subject matter of the claims.

Surprisingly it has been found that substituted N-(2-mercaptopyridin-3-yl)amides having the general formula (1) given below are suitable for the treatment of pain. It has further surprisingly been found that substituted N-(2-mercaptopyridin-3-yl)amides having the general formula (1) given below also have an excellent affinity for the KCNQ2/3 $K^+$ channel and are therefore suitable for the treatment of disorders or diseases which are at least partly mediated by KCNQ2/3 $K^+$ channels. The substituted N-(2-mercaptopyridin-3-yl)amides act here as modulators, i.e. agonists or antagonists, of the KCNQ2/3 $K^+$ channel.

The invention provides substituted N-(2-mercaptopyridin-3-yl)amides having the general formula (1)

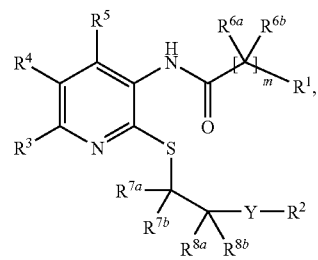

wherein m stands for 0, 1, 2 or 3;

$R^1$ stands for $C_{1-6}$ alkyl, saturated or unsaturated, branched or unbranched, unsubstituted or mono- or polysubstituted; $C_{3-10}$ cycloalkyl or heterocyclyl, each saturated or unsaturated, unsubstituted or mono- or polysubstituted; aryl or heteroaryl, each unsubstituted or mono- or polysubstituted;

with the proviso that if $R^1$ denotes heterocyclyl, the binding of the heterocyclyl to the higher-order general structure takes place via a carbon atom in the heterocyclyl;

$R^2$ stands for aryl or heteroaryl, each unsubstituted or mono- or polysubstituted;

Y is selected from the group consisting of —$(CR^{9a}R^{9b})$—, $S(=O)_2$, $S(=O)$, —S—, —O—, $C(=O)$;

$R^3$, $R^4$, $R^5$, $R^{6a}$, $R^{6b}$, $R^{7a}$, $R^{7b}$, $R^{8a}$, $R^{8b}$, $R^{9a}$ and $R^{9b}$ each stand independently of one another for H; F; Cl; Br; I; $NO_2$; $CF_3$; CN; OH; $OCF_3$; SH; $SCF_3$; $NH_2$; $C_{1-6}$ alkyl, O—$C_{1-6}$ alkyl, O—C(=O)—$C_{1-6}$ alkyl, S—$C_{1-6}$ alkyl, NH($C_{1-6}$ alkyl), N($C_{1-6}$ alkyl)$_2$, NH—C(=O)—$C_{1-6}$ alkyl, N(C(=O)—$C_{1-6}$ alkyl)$_2$ or C(=O)—$C_{1-6}$ alkyl, each saturated or unsaturated, branched or unbranched, unsubstituted or mono- or polysubstituted; $C_{3-7}$ cycloalkyl or heterocyclyl, each saturated or unsaturated, branched or unbranched, unsubstituted or mono- or polysubstituted;

wherein $R^{7a}$ can form with $R^{8a}$ a $C_{3-7}$ cycloalkyl radical, which can be saturated or unsaturated, unsubstituted or mono- or polysubstituted;

wherein "alkyl-substituted" stands for the substitution of one or more hydrogen atoms each independently of one another by F; Cl; Br; I; $NO_2$; $CF_3$; CN; $C_{1-8}$ alkyl; $C_{2-8}$ heteroalkyl; aryl; heteroaryl; $C_{3-10}$ cycloalkyl; heterocyclyl; $C_{1-8}$ alkyl- or $C_{2-8}$ heteroalkyl-bridged aryl, heteroaryl, $C_{3-10}$ cycloalkyl or heterocyclyl; CHO; C(=O)$C_{1-8}$ alkyl; C(=O)aryl; C(=O)heteroaryl; $CO_2H$; C(=O)O—$C_{1-8}$ alkyl; C(=O)O-aryl; C(=O)O-heteroaryl; $CONH_2$; C(=O)NH—$C_{1-8}$ alkyl; C(=O)N($C_{1-8}$ alkyl)$_2$; C(=O)NH-aryl; C(=O)N(aryl)$_2$; C(=O)NH-heteroaryl; C(=O)N(heteroaryl)$_2$; C(=O)N($C_{1-8}$ alkyl)(aryl); C(=O)N($C_{1-8}$ alkyl)(heteroaryl); C(=O)N(heteroaryl)(aryl); OH; O—$C_{1-8}$ alkyl; $OCF_3$; O—($C_{1-8}$ alkyl)-OH; O—($C_{1-8}$ alkyl)-O—$C_{1-8}$ alkyl; O-benzyl; O-aryl; O-heteroaryl; O—C(=O)$C_{1-8}$ alkyl; O—C(=O)aryl; O—C(=O)heteroaryl; $NH_2$; NH—$C_{1-8}$ alkyl; N($C_{1-8}$ alkyl)$_2$; NH—C(=O)$C_{1-8}$ alkyl; N($C_{1-8}$ alkyl)-C(=O)$C_{1-8}$ alkyl; N(C(=O)$C_{1-8}$ alkyl)$_2$; NH—C(=O)-aryl; NH—C(=O)-heteroaryl; SH; S—$C_{1-8}$ alkyl; $SCF_3$; S-benzyl; S-aryl; S-heteroaryl; $S(=O)_2C_{1-8}$ alkyl; $S(=O)_2$aryl; $S(=O)_2$heteroaryl; $S(=O)_2OH$; $S(=O)_2O$—$C_{1-8}$ alkyl; $S(=O)_2O$-aryl; $S(=O)_2O$-heteroaryl; $S(=O)_2$—NH—$C_{1-8}$ alkyl; $S(=O)_2$—NH-aryl; and $S(=O)_2$—NH—$C_{1-8}$-heteroaryl;

wherein "heterocyclyl-substituted" and "cycloalkyl-substituted" stands for the substitution of one or more hydrogen atoms each independently of one another by F; Cl; Br; I; $NO_2$; $CF_3$; =O; CN; $C_{1-8}$ alkyl; $C_{2-8}$ heteroalkyl; aryl; heteroaryl; $C_{3-10}$ cycloalkyl; heterocyclyl; $C_{1-8}$ alkyl- or $C_{2-8}$ heteroalkyl-bridged aryl, heteroaryl, $C_{3-10}$ cycloalkyl or heterocyclyl; CHO; C(=O)$C_{1-8}$ alkyl; C(=O)aryl; C(=O)heteroaryl; $CO_2H$; C(=O)O—$C_{1-8}$ alkyl; C(=O)O-aryl; C(=O)O-heteroaryl; $CONH_2$; C(=O)NH—$C_{1-8}$ alkyl; C(=O)N($C_{1-8}$ alkyl)$_2$; C(=O)NH-aryl; C(=O)N(aryl)$_2$; C(=O)NH-heteroaryl; C(=O)N(heteroaryl)$_2$; C(=O)N($C_{1-8}$ alkyl)(aryl); C(=O)N($C_{1-8}$ alkyl)(heteroaryl); C(=O)N(heteroaryl)(aryl); OH; O—$C_{1-8}$ alkyl; $OCF_3$; O—($C_{1-8}$ alkyl)-OH; O—($C_{1-8}$ alkyl)-O—$C_{1-8}$ alkyl; O-benzyl; O-aryl; O-heteroaryl; O—C(=O)$C_{1-8}$ alkyl; O—C(=O)aryl; O—C(=O)heteroaryl; $NH_2$; NH—$C_{1-8}$ alkyl; N($C_{1-8}$ alkyl)$_2$; NH—C(=O)$C_{1-8}$ alkyl; N($C_{1-8}$ alkyl)-C(=O)$C_{1-8}$ alkyl; N(C(=O)$C_{1-8}$ alkyl)$_2$; NH—C(=O)-aryl; NH—C(=O)-heteroaryl; SH; S—$C_{1-8}$ alkyl; $SCF_3$; S-benzyl; S-aryl; S-heteroaryl; $S(=O)_2C_{1-8}$ alkyl; $S(=O)_2$ aryl; $S(=O)_2$ heteroaryl; $S(=O)_2OH$; $S(=O)_2O$—$C_{1-8}$ alkyl; $S(=O)_2O$-aryl; $S(=O)_2O$-heteroaryl; $S(=O)_2$—NH—$C_{1-8}$ alkyl; $S(=O)_2$—NH-aryl; and $S(=O)_2$—NH—$C_{1-8}$ heteroaryl;

wherein "aryl-substituted" and "heteroaryl-substituted" stands for the substitution of one or more hydrogen atoms each independently of one another by F; Cl; Br; I; $NO_2$; $CF_3$; CN; $C_{1-8}$ alkyl; or $C_{2-8}$ heteroalkyl; aryl; heteroaryl; $C_{3-10}$ cycloalkyl; heterocyclyl; $C_{1-8}$ alkyl- or $C_{2-8}$ heteroalkyl-bridged aryl, heteroaryl, $C_{3-10}$ cycloalkyl or heterocyclyl; CHO; C(=O)$C_{1-8}$ alkyl; C(=O)aryl; C(=O)heteroaryl; $CO_2H$; C(=O)O—$C_{1-8}$ alkyl; C(=O)O-aryl; C(=O)O-heteroaryl; $CONH_2$; C(=O)NH—$CH_3$; C(=O)NH—$C_2H_5$; C(=O)N($C_{1-8}$ alkyl)$_2$; C(=O)NH-aryl; C(=O)N(aryl)$_2$; C(=O)NH-heteroaryl; C(=O)N(heteroaryl)$_2$; C(=O)N($C_{1-8}$ alkyl)(aryl); C(=O)N($C_{1-8}$ alkyl)(heteroaryl); C(=O)N(heteroaryl)(aryl); OH; O—$C_{1-8}$ alkyl; $OCF_3$; O—($C_{1-8}$ alkyl)-OH; O—($C_{1-8}$ alkyl)-O—$C_{1-8}$ alkyl; O-benzyl; O-aryl; O-heteroaryl; O—C(=O)$C_{1-8}$ alkyl; O—C(=O)aryl; O—C(=O)heteroaryl; $NH_2$, NH—$C_{1-8}$ alkyl; N($C_{1-8}$ alkyl)$_2$; NH—C(=O)$C_{1-8}$ alkyl; N($C_{1-8}$ alkyl)-C(=O)$C_{1-8}$ alkyl; N(C(=O)$C_{1-8}$ alkyl)$_2$; NH—C(=O)-aryl; NH—C(=O)-heteroaryl; SH; S—$C_{1-8}$ alkyl; $SCF_3$; S-benzyl; S-aryl; S-heteroaryl; $S(=O)_2C_{1-8}$ alkyl; $S(=O)_2$aryl; $S(=O)_2$heteroaryl; $S(=O)_2OH$; $S(=O)_2O$—$C_{1-8}$ alkyl; $S(=O)_2O$-aryl; $S(=O)_2O$-heteroaryl; $S(=O)_2$—NH—$C_{1-8}$ alkyl; $S(=O)_2$—NH-aryl; $S(=O)_2$—NH—$C_{1-8}$ heteroaryl;

in the form of the free compounds or salts of physiologically compatible acids or bases.

Within the meaning of this invention the expressions "alkyl" or "$C_{1-10}$ alkyl", "$C_{1-8}$ alkyl", "$C_{1-6}$ alkyl", "$C_{1-4}$ alkyl", "$C_{2-10}$ alkyl", "$C_{2-8}$ alkyl" and "$C_{4-10}$ alkyl" include acyclic saturated or unsaturated aliphatic hydrocarbon radicals, which can be branched or unbranched or unsubstituted or mono- or polysubstituted, having respectively 1 to 10 or 1 to 8 or 1 to 6 or 1 to 4 or 2 to 10 or 2 to 8 or 4 to 10 C atoms, i.e. $C_{1-10}$ alkanyls, $C_{2-10}$ alkenyls and $C_{2-10}$ alkynyls or $C_{1-8}$ alkanyls, $C_{2-8}$ alkenyls and $C_{2-8}$ alkynyls or $C_{1-6}$ alkanyls, $C_{2-6}$ alkenyls and $C_{2-6}$ alkynyls or $C_{1-4}$ alkanyls, $C_{2-4}$ alkenyls and $C_{2-4}$ alkynyls or $C_{2-10}$ alkanyls, $C_{2-10}$ alkenyls and $C_{2-10}$ alkynyls or $C_{2-8}$ alkanyls, $C_{2-8}$ alkenyls and $C_{2-8}$ alkynyls or $C_{4-10}$ alkanyls, $C_{4-10}$ alkenyls and $C_{4-10}$ alkynyls. Alkenyls have at least one C—C double bond and alkynyls have at least one C—C triple bond. Alkyl is preferably selected from the group comprising methyl, ethyl, n-propyl, 2-propyl, n-butyl, isobutyl, sec-butyl, tert-butyl, n-pentyl, isopentyl, neopentyl, n-hexyl, n-heptyl, n-octyl, n-nonyl, n-decyl, ethenyl (vinyl), ethynyl, propenyl (—$CH_2CH=CH_2$, —CH=CH—$CH_3$, —C(=$CH_2$)—$CH_3$), propynyl (—CH—C≡CH, —C≡C—$CH_3$), butenyl, butynyl, pentenyl, pentynyl, hexenyl and hexynyl, heptenyl, heptynyl, octenyl, octynyl, nonenyl, nonynyl, decenyl and decynyl.

For the purposes of this invention the expressions "cycloalkyl" or "$C_{3-10}$ cycloalkyl" and "$C_{3-7}$ cycloalkyl" denote cyclic aliphatic hydrocarbons having 3, 4, 5, 6, 7, 8, 9 or 10 carbon atoms or 3, 4, 5, 6 or 7 carbon atoms respectively, wherein the hydrocarbons can be saturated or unsaturated (but not aromatic), unsubstituted or mono- or polysubstituted. The binding of the cycloalkyl to the higher-order general structure can be made via any desired and possible ring member of the cycloalkyl radical. The cycloalkyl radicals can also be fused to further saturated, (partially) unsaturated, (hetero) cyclic, aromatic or heteroaromatic ring systems, i.e. to cycloalkyl, heterocyclyl, aryl or heteroaryl, which can in turn be unsubstituted or mono- or polysubstituted. Examples of such ring systems are chromanyl, tetrahydronaphthyl and decahydronaphthyl. The cycloalkyl radicals can further be singly or multiply bridged, as for example in the case of adamantyl, bicyclo[2.2.1]heptyl or bicyclo[2.2.2]octyl. Cycloalkyl is preferably selected from the group comprising cyclopropyl, cyclobutyl, cyclopentyl, cyclohexyl, cycloheptyl, cyclooctyl, cyclononyl, cyclodecyl, adamantyl,

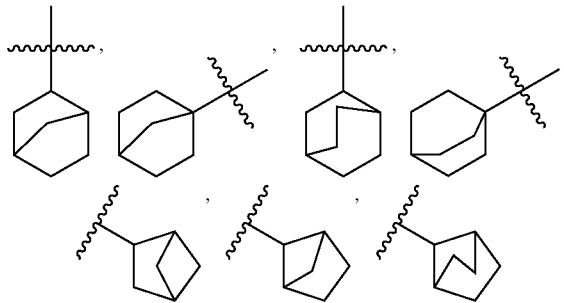

cyclopentenyl, cyclohexenyl, cycloheptenyl and cyclooctenyl.

The term "heterocyclyl" or "heterocycloalkyl" includes aliphatic saturated or unsaturated (but not aromatic) cycloalkyls having three to ten, i.e. 3, 4, 5, 6, 7, 8, 9 or 10 ring members, in which at least one, optionally also two or three, carbon atoms are replaced by a heteroatom or a heteroatom group selected independently of one another from the group consisting of O, S, N, NH and N($C_{1-8}$ alkyl), preferably N(CH$_3$), wherein the ring members can be unsubstituted or mono- or polysubstituted. The binding of the heterocyclyl to the higher-order general structure can be made via any desired and possible ring member of the heterocyclyl radical. The heterocyclyl radicals can also be fused to further saturated, (partially) unsaturated, (hetero)cyclic or aromatic or heteroaromatic ring systems, i.e. to cycloalkyl, heterocyclyl, aryl or heteroaryl, which can in turn be unsubstituted or mono- or polysubstituted. Preferred are heterocyclyl radicals from the group comprising azetidinyl, aziridinyl, azepanyl, azocanyl, diazepanyl, dithiolanyl, dihydroquinolinyl, dihydropyrrolyl, dioxanyl, dioxolanyl, dihydroindenyl, dihydropyridinyl, dihydrofuranyl, dihydroisoquinolinyl, dihydroindolinyl, dihydroisoindolyl, imidazolidinyl, isoxazolidinyl, morpholinyl, oxiranyl, oxetanyl, pyrrolidinyl, piperazinyl, piperidinyl, pyrazolidinyl, pyranyl, tetrahydropyrrolyl, tetrahydropyranyl, tetrahydroquinolinyl, tetrahydroisoquinolinyl, tetrahydroindolinyl, tetrahydrofuranyl, tetrahydropyridinyl, tetrahydrothiophenyl, tetrahydropyridoindolyl, tetrahydronaphthyl, tetrahydrocarbolinyl, tetrahydroisoxazolopyridinyl, thiazolidinyl and thiomorpholinyl.

Within the meaning of this invention, the term "aryl" denotes aromatic hydrocarbons having up to 14 ring members, inter alia phenyls and naphthyls. Each aryl radical can be present in unsubstituted or mono- or polysubstituted form, wherein the aryl substituents can be identical or different and can be at any desired and possible position of the aryl. The binding of the aryl to the higher-order general structure can be made via any desired and possible ring member of the aryl radical. The aryl radicals can also be fused to further saturated, (partially) unsaturated, (hetero)cyclic, aromatic or heteroaromatic ring systems, i.e. to cycloalkyl, heterocyclyl, aryl or heteroaryl, which can in turn be unsubstituted or mono- or polysubstituted. Examples of fused aryl radicals are benzodioxolanyl and benzodioxanyl. Aryl is preferably selected from the group including phenyl, 1-naphthyl and 2-naphthyl, each of which can be unsubstituted or mono- or polysubstituted. A particularly preferred aryl is phenyl, unsubstituted or mono- or polysubstituted.

The term "heteroaryl" stands for a 5- or 6-membered cyclic aromatic radical containing at least 1, optionally also 2, 3, 4 or 5 heteroatoms, wherein the heteroatoms can each be selected independently of one another from the group S, N or O and the heteroaryl radical can be unsubstituted or mono- or polysubstituted; if the heteroaryl is substituted, the substituents can be identical or different and can be at any desired and possible position of the heteroaryl. The binding to the higher-order general structure can be made via any desired and possible ring member of the heteroaryl radical. The heteroaryl can also be part of a bicyclic or polycyclic system having up to 14 ring members, wherein the ring system can be formed with further saturated, (partially) unsaturated, (hetero)cyclic or aromatic or heteroaromatic rings, i.e. with cycloalkyl, heterocyclyl, aryl or heteroaryl, which can in turn be unsubstituted or mono- or polysubstituted. The heteroaryl radical is preferably selected from the group comprising benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazolyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl. Furyl, pyridyl and thienyl are particularly preferred.

In connection with "alkyl", the term "mono- or polysubstituted" within the meaning of this invention is understood to mean the single or multiple, e.g. two, three or four times, substitution of one or more hydrogen atoms each independently of one another by substituents selected from the group comprising F; Cl; Br; I; NO$_2$; CF$_3$; CN; $C_{1-8}$ alkyl; $C_{2-8}$ heteroalkyl; aryl; heteroaryl; $C_{3-10}$ cycloalkyl; heterocyclyl; $C_{1-8}$ alkyl- or $C_{2-8}$ heteroalkyl-bridged aryl, heteroaryl, $C_{3-10}$ cycloalkyl or heterocyclyl; CHO; C(=O)$C_{1-8}$ alkyl; C(=O) aryl; C(=O)heteroaryl; CO$_2$H; C(=O)O—$C_{1-8}$ alkyl; C(=O)O-aryl; C(=O)O-heteroaryl; CONH$_2$; C(=O)NH—$C_{1-8}$ alkyl; C(=O)N($C_{1-8}$ alkyl)$_2$; C(=O)NH-aryl; C(=O)N(aryl)$_2$; C(=O)NH-heteroaryl; C(=O)N(heteroaryl)$_2$; C(=O)N($C_{1-8}$ alkyl)(aryl); C(=O)N($C_{1-8}$ alkyl)(heteroaryl); C(=O)N(heteroaryl)(aryl); OH; O—$C_{1-8}$ alkyl; OCF$_3$; O—($C_{1-8}$ alkyl)-OH; O—($C_{1-8}$ alkyl)-O—$C_{1-8}$ alkyl; O-benzyl; O-aryl; O-heteroaryl; O—C(=O)$C_{1-8}$ alkyl; O—C(=O)aryl; O—C(=O)heteroaryl; NH$_2$, NH—$C_{1-8}$ alkyl; N($C_{1-8}$ alkyl)$_2$; NH—C(=O)$C_{1-8}$ alkyl; N($C_{1-8}$ alkyl)-C(=O)$C_{1-8}$ alkyl; N(C(=O)$C_{1-8}$ alkyl)$_2$; NH—C(=O)-aryl; NH—C(=O)-heteroaryl; SH; S—$C_{1-8}$ alkyl; SCF$_3$; S-benzyl; S-aryl; S-heteroaryl; S(=O)$_2$$C_{1-8}$ alkyl; S(=O)$_2$ aryl; S(=O)$_2$ heteroaryl; S(=O)$_2$OH; S(=O)$_2$O—$C_{1-8}$ alkyl; S(=O)$_2$O-aryl; S(=O)$_2$O-heteroaryl; S(=O)$_2$—NH—$C_{1-8}$ alkyl; S(=O)$_2$—NH-aryl; and S(=O)$_2$—NH—$C_{1-8}$ heteroaryl; wherein polysubstituted radicals are understood to mean radicals which are substituted multiple times, for example two, three or four times, at different or the same atoms, for example substituted three times at the same C atom, as in the case of CF$_3$ or CH$_2$CF$_3$, or at different sites, as in the case of CH(OH)—CH=CH—CHCl$_2$. A substituent can in turn itself optionally be mono- or polysubstituted. The polysubstitution can be performed with identical or different substituents.

Preferred "alkyl" substituents are selected from the group comprising F; Cl; Br; I; NO$_2$; CH$_2$CF$_3$; CF$_3$; CN; C$_{1-8}$ alkyl; C$_{2-8}$ heteroalkyl; phenyl; naphthyl; pyridyl; thienyl; furyl; C$_{3-10}$ cycloalkyl; heterocyclyl; C$_{1-8}$ alkyl- or C$_{2-8}$ heteroalkyl-bridged phenyl, naphthyl, pyridyl, thienyl, furyl, C$_{3-10}$ cycloalkyl or heterocyclyl; CHO; C(=O)C$_{1-8}$ alkyl; CO$_2$H; C(=O)O—C$_{1-8}$ alkyl; CONH$_2$; C(=O)NH—C$_{1-8}$ alkyl; C(=O)N(C$_{1-8}$ alkyl)$_2$; OH; O—C$_{1-8}$ alkyl; OCF$_3$; O—(C$_{1-8}$ alkyl)-OH; O—(C$_{1-8}$ alkyl)-O—C$_{1-8}$ alkyl; O-benzyl; O-phenyl; O-heteroaryl; O—C(=O)C$_{1-8}$ alkyl; NH$_2$, NH—C$_{1-8}$ alkyl; N(C$_{1-8}$ alkyl)$_2$; NH—C(=O)C$_{1-8}$ alkyl; N(C$_{1-8}$ alkyl)-C(=O)C$_{1-8}$ alkyl; N(C(=O)C$_{1-8}$ alkyl)$_2$; SH; S—C$_{1-8}$ alkyl; SCF$_3$; S-benzyl; S-phenyl; S-heteroaryl; S(=O)$_2$C$_{1-8}$ alkyl; S(=O)$_2$OH; S(=O)$_2$O—C$_{1-8}$ alkyl; S(=O)$_2$—NH—C$_{1-8}$ alkyl.

In connection with "heterocyclyl-substituted" and "cycloalkyl-substituted" the term "mono- or polysubstituted" within the meaning of this invention is understood to mean the single or multiple, e.g. two, three or four times, substitution of one or more hydrogen atoms each independently of one another by substituents selected from the group comprising F; Cl; Br; I; NO$_2$; CF$_3$; =O; CN; C$_{1-8}$ alkyl; C$_{2-8}$ heteroalkyl; aryl; heteroaryl; C$_{3-10}$ cycloalkyl; heterocyclyl; C$_{1-8}$ alkyl- or C$_{2-8}$ heteroalkyl-bridged aryl, heteroaryl, C$_{3-10}$ cycloalkyl or heterocyclyl; CHO; C(=O)C$_{1-8}$ alkyl; C(=O)aryl; C(=O)heteroaryl; CO$_2$H; C(=O)O—C$_{1-8}$ alkyl; C(=O)O-aryl; C(=O)O-heteroaryl; CONH$_2$; C(=O)NH—C$_{1-8}$ alkyl; C(=O)N(C$_{1-8}$ alkyl)$_2$; C(=O)NH-aryl; C(=O)N(aryl)$_2$; C(=O)NH-heteroaryl; C(=O)N(heteroaryl)$_2$; C(=O)N(C$_{1-8}$ alkyl)(aryl); C(=O)N(C$_{1-8}$ alkyl)(heteroaryl); C(=O)N(heteroaryl)(aryl); OH; O—C$_{1-8}$ alkyl; OCF$_3$; O—(C$_{1-8}$ alkyl)-OH; O—(C$_{1-8}$ alkyl)-O—C$_{1-8}$ alkyl; O-benzyl; O-aryl; O-heteroaryl; O—C(=O)C$_{1-8}$ alkyl; O—C(=O)aryl; O—C(=O)heteroaryl; NH$_2$, NH—C$_{1-8}$ alkyl; N(C$_{1-8}$ alkyl)$_2$; NH—C(=O)C$_{1-8}$ alkyl; N(C$_{1-8}$ alkyl)-C(=O)C$_{1-8}$ alkyl; N(C(=O)C$_{1-8}$ alkyl)$_2$; NH—C(=O)-aryl; NH—C(=O)-heteroaryl; SH; S—C$_{1-8}$ alkyl; SCF$_3$; S-benzyl; S-aryl; S-heteroaryl; S(=O)$_2$C$_{1-8}$ alkyl; S(=O)$_2$ aryl; S(=O)$_2$ heteroaryl; S(=O)$_2$OH; S(=O)$_2$O—C$_{1-8}$ alkyl; S(=O)$_2$O-aryl; S(=O)$_2$O-heteroaryl; S(=O)$_2$—NH—C$_{1-8}$ alkyl; S(=O)$_2$—NH-aryl; and S(=O)$_2$—NH—C$_{1-8}$ heteroaryl; wherein polysubstituted radicals are understood to mean radicals which are substituted multiple times, for example two, three or four times, at different or the same atoms, for example substituted twice at the same C atom, as in the case of 1,1-difluorocyclohexyl, or at different sites, as in the case of 1,2-difluorocyclohexyl. A substituent can in turn itself optionally be mono- or polysubstituted. The polysubstitution can be performed with identical or different substituents.

Preferred "heterocyclyl" and "cycloalkyl" substituents are selected from the group comprising F; Cl; Br; I; NO$_2$; CH$_2$CF$_3$; OF$_3$; ON; C$_{1-8}$ alkyl; C$_{2-8}$ heteroalkyl; phenyl; naphthyl; pyridyl; thienyl; furyl; C$_{3-10}$ cycloalkyl; heterocyclyl; C$_{1-8}$ alkyl- or C$_{2-8}$ heteroalkyl-bridged phenyl, naphthyl, pyridyl, thienyl, furyl, C$_{3-10}$ cycloalkyl or heterocyclyl; CHO; C(=O)C$_{1-8}$ alkyl; CO$_2$H; C(=O)O—C$_{1-8}$ alkyl; CONH$_2$; C(=O)NH—C$_{1-8}$ alkyl; C(=O)N(C$_{1-8}$ alkyl)$_2$; OH; =O; O—C$_{1-8}$ alkyl; OCF$_3$; O—(C$_{1-8}$ alkyl)-OH; O—(C$_{1-8}$ alkyl)-O—C$_{1-8}$ alkyl; O-benzyl; O-phenyl; O-heteroaryl; O—C(=O)C$_{1-8}$ alkyl; NH$_2$; NH—C$_{1-8}$ alkyl; N(C$_{1-8}$ alkyl)$_2$; NH—C(=O)C$_{1-8}$ alkyl; N(C$_{1-8}$ alkyl)-C(=O)C$_{1-8}$ alkyl; N(C(=O)C$_{1-8}$ alkyl)$_2$; SH; S—C$_{1-8}$ alkyl; SCF$_3$; S-benzyl; S-phenyl; S-heteroaryl; S(=O)$_2$C$_{1-8}$ alkyl; S(=O)$_2$OH; S(=O)$_2$O—C$_{1-8}$ alkyl; S(=O)$_2$—NH—C$_{1-8}$ alkyl.

In connection with "aryl" and "heteroaryl" the expression "mono- or polysubstituted" within the meaning of this invention is understood to mean the single or multiple, e.g. two, three or four times, substitution of one or more hydrogen atoms in the ring system, each independently of one another with substituents selected from the group comprising F; Cl; Br; I; NO$_2$; CF$_3$; CN; C$_{1-8}$ alkyl; or C$_{2-8}$ heteroalkyl; aryl; heteroaryl; C$_{3-10}$ cycloalkyl; heterocyclyl; C$_{1-8}$ alkyl- or C$_{2-8}$ heteroalkyl-bridged aryl, heteroaryl, C$_{3-10}$ cycloalkyl or heterocyclyl; CHO; C(=O)C$_{1-8}$ alkyl; C(=O)aryl; C(=O)heteroaryl; CO$_2$H; C(=O)O—C$_{1-8}$ alkyl; C(=O)O-aryl; C(=O)O-heteroaryl; CONH$_2$; C(=O)NH—CH$_3$; C(=O)NH—C$_2$H$_5$; C(=O)N(C$_{1-8}$ alkyl)$_2$; C(=O)NH-aryl; C(=O)N(aryl)$_2$; C(=O)NH-heteroaryl; C(=O)N(heteroaryl)$_2$; C(=O)N(C$_{1-8}$ alkyl)(aryl); C(=O)N(C$_{1-8}$ alkyl)(heteroaryl); C(=O)N(heteroaryl)(aryl); OH; O—C$_{1-8}$ alkyl; OCF$_3$; O—(C$_{1-8}$ alkyl)-OH; O—(C$_{1-8}$ alkyl)-O—C$_{1-8}$ alkyl; O-benzyl; O-aryl; O-heteroaryl; O—C(=O)C$_{1-8}$ alkyl; O—C(=O)aryl; O—C(=O)heteroaryl; NH$_2$, NH—C$_{1-8}$ alkyl; N(C$_{1-8}$ alkyl)$_2$; NH—C(=O)C$_{1-8}$ alkyl; N(C$_{1-8}$ alkyl)-C(=O)C$_{1-8}$ alkyl; N(C(=O)C$_{1-8}$ alkyl)$_2$; NH—C(=O)-aryl; NH—C(=O)-heteroaryl; SH; S—C$_{1-8}$ alkyl; SCF$_3$; S-benzyl; S-aryl; S-heteroaryl; S(=O)$_2$C$_{1-8}$ alkyl; S(=O)$_2$ aryl; S(=O)$_2$ heteroaryl; S(=O)$_2$OH; S(=O)$_2$O—C$_{1-8}$ alkyl; S(=O)$_2$O-aryl; S(=O)$_2$O-heteroaryl; S(=O)$_2$—NH—C$_{1-8}$ alkyl; S(=O)$_2$—NH-aryl; S(=O)$_2$—NH—C$_{1-8}$ heteroaryl; at one or optionally different atoms, wherein a substituent can in turn itself optionally be mono- or polysubstituted. The polysubstitution is performed with identical or with different substituents.

Preferred "aryl" and "heteroaryl" substituents are F; Cl; Br; I; NO$_2$; CH$_2$CF$_3$; CF$_3$; CN; C$_{1-8}$ alkyl; C$_{2-8}$ heteroalkyl; phenyl; naphthyl; pyridyl; thienyl; furyl; C$_{3-10}$ cycloalkyl; heterocyclyl; C$_{1-8}$ alkyl- or C$_{2-8}$ heteroalkyl-bridged phenyl, naphthyl, pyridyl, thienyl, furyl, C$_{3-10}$ cycloalkyl or heterocyclyl; CHO; C(=O)C$_{1-8}$ alkyl; CO$_2$H; C(=O)O—C$_{1-8}$ alkyl; CONH$_2$; C(=O)NH—CH$_3$; C(=O)NH—C$_2$H$_5$; C(=O)N(C$_{1-8}$ alkyl)$_2$; OH; O—C$_{1-8}$ alkyl; OCF$_3$; O—(C$_{1-8}$ alkyl)-OH; O—(C$_{1-8}$ alkyl)-O—C$_{1-8}$ alkyl; O-benzyl; O-phenyl; O-heteroaryl; C(=O)C$_{1-8}$ alkyl; NH$_2$, NH—C$_{1-8}$ alkyl; N(C$_{1-8}$ alkyl)$_2$; NH—C(=O)C$_{1-8}$ alkyl; N(C$_{1-8}$ alkyl)-C(=O)C$_{1-8}$ alkyl; N(C(=O)C$_{1-8}$ alkyl)$_2$; SH; S—C$_{1-8}$ alkyl; SCF$_3$; S-benzyl; S-phenyl; S-heteroaryl; S(=O)$_2$C$_{1-8}$ alkyl; S(=O)$_2$OH; S(=O)$_2$O—C$_{1-8}$ alkyl; S(=O)$_2$—NH—C$_{1-8}$ alkyl.

The compounds according to the invention are defined by substituents, for example by R$^1$, R$^2$ and R$^3$ (1$^{st}$ generation substituents), which are in turn optionally substituted (2$^{nd}$ generation substituents). Depending on the definition, these substituents of the substituents can themselves be substituted again (3$^{rd}$ generation substituents). For example, if R$^1$=aryl (1$^{st}$ generation substituent), then aryl can itself be substituted, e.g. with C$_{1-8}$ alkyl (2$^{nd}$ generation substituent). This gives the functional group aryl C$_{1-8}$ alkyl. C$_{1-8}$ alkyl can then itself be substituted again, for example with Cl (3$^{rd}$ generation substituent). This then gives in total the functional group aryl C$_{1-8}$ alkyl Cl.

In a preferred embodiment the 3$^{rd}$ generation substituents cannot, however, be substituted again, i.e. there are then no 4$^{th}$ generation substituents.

In another preferred embodiment the 2$^{nd}$ generation substituents cannot be substituted again, i.e. there are then no 3$^{rd}$ generation substituents either. In other words, in this embodiment or in the case of the general formula (1) the functional groups for R$^1$ to R$^5$ can each optionally be substituted, but the various substituents cannot then themselves be substituted again.

In some cases the compounds according to the invention are defined by substituents which are or which carry an aryl or heteroaryl radical, each unsubstituted or mono- or polysubstituted, or which together with the carbon atom(s) or heteroatom(s) binding them as ring member or ring members form a ring, for example an aryl or heteroaryl, each unsubstituted or mono- or polysubstituted. Both these aryl or heteroaryl radicals and the aromatic ring systems formed in this way can optionally be fused to $C_{3-10}$ cycloalkyl or heterocyclyl, each saturated or unsaturated, i.e. to a $C_{3-10}$ cycloalkyl such as cyclopentyl or a heterocyclyl such as morpholinyl, wherein the $C_{3-10}$ cycloalkyl or heterocyclyl radicals fused in this way can themselves be unsubstituted or mono- or polysubstituted.

In some cases the compounds according to the invention are defined by substituents which are or which carry a $C_{3-10}$ cycloalkyl or heterocyclyl radical, each unsubstituted or mono- or polysubstituted, or which together with the carbon atom(s) or heteroatom(s) binding them as ring member or ring members form a ring, for example a $C_{3-10}$ cycloalkyl or heterocyclyl, each unsubstituted or mono- or polysubstituted. Both these $C_{3-10}$ cycloalkyl or heterocyclyl radicals and the aliphatic ring systems formed can optionally be fused to aryl or heteroaryl, i.e. to an aryl such as phenyl or to a heteroaryl such as pyridyl, wherein the aryl or heteroaryl radical can itself be unsubstituted or mono- or polysubstituted.

In the context of the present invention, the symbol

used in formulae represents a linking of a corresponding radical to the higher-order general structure.

Within the meaning of this invention the term "salt formed with a physiologically compatible acid" is understood to mean salts of the individual active ingredient with inorganic or organic acids which are physiologically—particularly when used in humans and/or mammals—compatible. Hydrochloride is particularly preferred. Examples of physiologically compatible acids are: hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, saccharinic acid, monomethyl sebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, hippuric acid, phosphoric acid and/or aspartic acid. Citric acid and hydrochloric acid are particularly preferred.

Physiologically compatible salts with cations or bases are salts of the individual compound as anion with at least one, preferably inorganic, cation, which are physiologically—particularly when used in humans and/or mammals—compatible. Particularly preferred are the salts of the alkali and alkaline-earth metals, but also ammonium salts, but in particular (mono) or (di)sodium, (mono) or (di)potassium, magnesium or calcium salts.

In a preferred embodiment of the compounds according to the invention m stands for 0 or 1, particularly preferably for 1.

In a likewise preferred embodiment of the compounds according to the invention the radical $R^1$ stands for $C_{1-6}$ alkyl, saturated or unsaturated, branched or unbranched, unsubstituted or mono- or polysubstituted with one or more substituents each selected independently of one another from the group consisting of F, Cl, Br, I, $NO_2$, $CF_3$, CN, OH, $OCF_3$, C(=O)—OH, SH, S—$C_{1-8}$ alkyl, $SCF_3$, $S(=O)_2OH$, $NH_2$, $C_{1-8}$ alkyl, O—$C_{1-8}$ alkyl, NH—$C_{1-8}$ alkyl, $N(C_{1-8}$ alkyl$)_2$, wherein the aforementioned alkyl radicals can each in turn be saturated or unsaturated, branched or unbranched, unsubstituted or mono- or polysubstituted with one or more substituents each selected independently of one another from the group consisting of F, Cl, Br, I, O—$C_{1-8}$ alkyl, OH and $OCF_3$; $C_{3-10}$ cycloalkyl or heterocyclyl, each saturated or unsaturated, unsubstituted or mono- or polysubstituted with one or more substituents each selected independently of one another from the group consisting of F, Cl, Br, I, $NO_2$, $CH_2CF_3$, $CF_3$, CN, CHO, $CO_2H$, SH, $SCF_3$, $S(=O)_2OH$, OH, =O, $OCF_3$, $NH_2$, C(=O)—$NH_2$, $C_{1-8}$ alkyl, $C_{2-8}$ heteroalkyl, NH—$C_{1-8}$ alkyl, $N(C_{1-8}$ alkyl$)_2$, O—$C_{1-8}$ alkyl, C(=O)$C_{1-8}$ alkyl, C(=O)O—$C_{1-8}$ alkyl, O—C(=O)$C_{1-8}$ alkyl, C(=O)NH—$C_{1-8}$ alkyl, C(=O)N($C_{1-8}$ alkyl$)_2$, NH—C(=O)$C_{1-8}$ alkyl, N($C_{1-8}$ alkyl)-C(=O)$C_{1-8}$ alkyl, N(C(=O)$C_{1-8}$ alkyl$)_2$, S—$C_{1-8}$ alkyl, $S(=O)_2$O—$C_{1-8}$ alkyl, benzyl, phenyl, pyridyl, thienyl and furyl; wherein the aforementioned alkyl and heteroalkyl radicals can each be saturated or unsaturated, branched or unbranched, unsubstituted or mono- or polysubstituted with one or more substituents each selected independently of one another from the group consisting of O—$C_{1-4}$ alkyl and OH; and wherein benzyl, phenyl, pyridyl, thienyl and furyl can each be unsubstituted or mono- or polysubstituted with one or more substituents each selected independently of one another from the group consisting of F, Cl, Br, I, CN, $C_{1-4}$ alkyl, O—$C_{1-4}$ alkyl, $CF_3$, OH and $OCF_3$;

aryl or heteroaryl, each unsubstituted or mono- or polysubstituted with one or more substituents each selected independently of one another from the group consisting of F, Cl, Br, I, $NO_2$, $OH_2CF_3$, $CF_3$, CN, CHO, $CO_2H$, SH, $SCF_3$, $S(=O)_2OH$, OH, $OCF_3$, $NH_2$, C(=O)—$NH_2$, $C_{1-8}$ alkyl, $C_{2-8}$ heteroalkyl, NH—$C_{1-8}$ alkyl, $N(C_{1-8}$ alkyl$)_2$, O—$C_{1-8}$ alkyl, C(=O)$C_{1-8}$ alkyl, C(=O)O—$C_{1-8}$ alkyl, O—C(=O) $C_{1-8}$ alkyl, C(=O)NH—$C_{1-8}$ alkyl, C(=O)N($C_{1-8}$ alkyl$)_2$, NH—C(=O)$C_{1-8}$ alkyl, N($C_{1-8}$ alkyl)-C(=O)$C_{1-8}$ alkyl, N(C(=O)$C_{1-8}$ alkyl$)_2$, S—$C_{1-8}$ alkyl, $S(=O)_2$O—$C_{1-8}$ alkyl, $C_{3-10}$ cycloalkyl and heterocyclyl, benzyl, phenyl, pyridyl, thienyl and furyl; wherein the aforementioned alkyl and heteroalkyl radicals can each be saturated or unsaturated, branched or unbranched, unsubstituted or mono- or polysubstituted with one or more substituents each selected independently of one another from the group consisting of O—$C_{1-4}$ alkyl and OH; wherein $C_{3-10}$ cycloalkyl or heterocyclyl can each be saturated or unsaturated, unsubstituted or mono- or polysubstituted with one or more substituents each selected independently of one another from the group consisting of O—$C_{1-4}$ alkyl, =O and OH; and wherein benzyl, phenyl, pyridyl, thienyl and furyl can each be unsubstituted or mono- or polysubstituted with one or more substituents each selected independently of one another from the group consisting of F, Cl, Br, I, CN, $C_{1-4}$ alkyl, O—$C_{1-4}$ alkyl, $CF_3$, OH and $OCF_3$.

In a further preferred embodiment the radical $R^1$ stands for aryl or heteroaryl, each unsubstituted or mono- or polysubstituted with one or more substituents each selected independently of one another from the group consisting of F, Cl, Br, I, $NO_2$, $CH_2CF_3$, $CF_3$, CN, CHO, $CO_2H$, SH, $SCF_3$, $S(=O)_2OH$, OH, $OCF_3$, $NH_2$, C(=O)—$NH_2$, $C_{1-8}$ alkyl, $C_{2-8}$ heteroalkyl, NH—$C_{1-8}$ alkyl, $N(C_{1-8}$ alkyl$)_2$, O—$C_{1-8}$ alkyl, C(=O)$C_{1-8}$ alkyl, C(=O)O—$C_{1-8}$ alkyl, O—C(=O) $C_{1-8}$ alkyl, C(=O)NH—$C_{1-8}$ alkyl, C(=O)N($C_{1-8}$ alkyl$)_2$, NH—C(=O)$C_{1-8}$ alkyl, N($C_{1-8}$ alkyl)-C(=O)$C_{1-8}$ alkyl, N(C(=O)$C_{1-8}$ alkyl$)_2$, S—$C_{1-8}$ alkyl, $S(=O)_2$O—$C_{1-8}$ alkyl, $C_{3-10}$ cycloalkyl and heterocyclyl, benzyl, phenyl, pyridyl, thienyl and furyl; wherein the aforementioned alkyl and heteroalkyl radicals can each be saturated or unsaturated, branched or unbranched, unsubstituted or mono- or polysubstituted with one or more substituents each selected independently of one another from the group consisting of O—$C_{1-4}$ alkyl and OH; wherein $C_{3-10}$ cycloalkyl or heterocyclyl can each be saturated or unsaturated, unsubstituted or mono- or polysubstituted with one or more substituents each selected independently of one another from the group consisting of O—$C_{1-4}$ alkyl, =O and OH; and wherein benzyl, phenyl, pyridyl, thienyl and furyl can each be unsubstituted or mono- or polysubstituted with one or more substituents each selected independently of one another from the group consisting of F, Cl, Br, I, CN, $C_{1-4}$ alkyl, O—$C_{1-4}$ alkyl, $CF_3$, OH and $OCF_3$.

The radical $R^1$ preferably stands for phenyl, naphthyl, biphenyl, benzofuranyl, benzothienyl, furyl, imidazolyl, indolyl, oxazolyl, oxadiazolyl, pyrimidinyl, pyridazinyl, pyrazinyl, pyrrolyl, pyrazolyl, pyridyl, thienyl, thiazolyl, each unsubstituted or mono- or polysubstituted with one or more substituents each selected independently of one another from the group consisting of F, Cl, Br, I, $NO_2$, $CF_3$, CN, $CH_2CF_3$, C(=O)—OH, SH, $SCF_3$, $S(=O)_2OH$, $OCF_3$, OH, $NH_2$, C(=O)$NH_2$, $C_{1-8}$ alkyl, O—$C_{1-8}$ alkyl, NH—$C_{1-8}$ alkyl, N($C_{1-8}$ alkyl)$_2$, wherein alkyl can be saturated or unsaturated, branched or unbranched, unsubstituted or mono- or polysubstituted with one or more substituents each selected independently of one another from the group consisting of O-methyl and OH, C(=O)$C_{1-8}$ alkyl, C(=O)O—$C_{1-8}$ alkyl, O—C(=O)—$C_{1-8}$ alkyl, C(=O)NH—$C_{1-8}$ alkyl, C(=O)N($C_{1-8}$ alkyl)$_2$, NH—C(=O)$C_{1-8}$ alkyl, N($C_{1-8}$ alkyl)-C(=O)$C_{1-8}$ alkyl, N(C(=O)$C_{1-8}$ alkyl)$_2$, S—$C_{1-8}$ alkyl, $S(=O)_2$O—$C_{1-8}$ alkyl, wherein alkyl can be saturated or unsaturated, branched or unbranched, unsubstituted, cyclopentyl, cyclohexyl, adamantyl, pyrrolidinyl, piperidinyl, 4-methylpiperazinyl, piperazinyl or morpholinyl, each unsubstituted, benzyl, phenyl or pyridyl, wherein benzyl, phenyl or pyridyl are each unsubstituted or mono-, di- or trisubstituted with one, two or three substituents each selected independently of one another from the group consisting of F, Cl, Br, I, CN, $C_{1-8}$ alkyl, O—$C_{1-8}$ alkyl, $CF_3$, OH and $OCF_3$.

$R^1$ particularly preferably stands for phenyl, pyridyl or thienyl, each unsubstituted or mono- or polysubstituted with one or more substituents each selected independently of one another from the group consisting of F, Cl, Br, I, $NO_2$, $CF_3$, CN, methyl, ethyl, n-propyl, isopropyl, cyclopropyl, n-butyl, sec-butyl, tert-butyl, $CH_2CF_3$, C(=O)-methyl, C(=O)-ethyl, C(=O)—OH, C(=O)—O-methyl, C(=O)—O-ethyl, C(=O)—$NH_2$, C(=O)—N(methyl)$_2$, C(=O)—N(ethyl)$_2$, C(=O)—NH-methyl, C(=O)—NH-ethyl, C(=O)—N(methyl)(ethyl), OH, O-methyl, O-ethyl, O—$(CH_2)_2$—O—$CH_3$, O—$(CH_2)_2$—OH, $OCF_3$, O—C(=O)-methyl, O—C(=O)-ethyl, $NR^aR^b$, wherein $R^a$ and $R^b$ are selected independently of one another from the group consisting of H, methyl, ethyl, $(CH_2)_2$—O—$CH_3$ and $(CH_2)_2$—OH or $R^a$ and $R^b$ together with the nitrogen atom linking them form a pyrrolidinyl, piperidinyl, 4-methylpiperazinyl or morpholinyl, NHC(=O)-methyl, NHC(=O)-ethyl, SH, $SCF_3$, S-methyl, S-ethyl, $S(=O)_2OH$, $S(=O)_2$O-methyl, benzyl, phenyl, pyridyl, wherein benzyl, phenyl, pyridyl are each unsubstituted or mono-, di- or trisubstituted with one, two or three substituents each selected independently of one another from the group consisting of F, Cl, Br, I, CN, methyl, ethyl, $CF_3$, OH, O-methyl and $OCF_3$.

$R^1$ most particularly preferably stands for phenyl, pyridyl or thienyl, each unsubstituted or mono- or di- or trisubstituted with one, two or three substituents each selected independently of one another from the group consisting of F, Cl, Br, I, $NO_2$, $CF_3$, CN, methyl, ethyl, C(=O)-methyl, OH, O-methyl, O—$(CH_2)_2$—O—$CH_3$, $OCF_3$, O—C(=O)-methyl, $NH_2$, NH—C(=O)-methyl, N(methyl)$_2$, morpholinyl, S-methyl, $SCF_3$, benzyl and phenyl, each unsubstituted.

In a further preferred embodiment m stands for the number 1, wherein $R^1$ has the meaning according to one of the aforementioned embodiments, but is preferably a thienyl, phenyl, $C_{3-8}$ alkyl radical, which can be saturated or unsaturated, unsubstituted or mono- or polysubstituted, or a monocyclic or bicyclic $C_{3-8}$ cycloalkyl radical, which can be saturated or unsaturated (but not aromatic), unsubstituted or mono- or polysubstituted.

Preferred examples of these cycloalkyl radicals are cyclopentyl, cyclohexyl, cycloheptyl, cyclooctyl, adamantyl, dihydropyranyl, tetrahydrofuranyl or

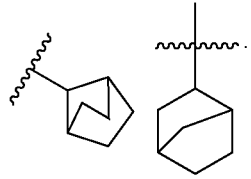

In a further preferred embodiment m stands for the number 2, wherein $R^1$ has the meaning according to one of the aforementioned embodiments but preferably stands for phenyl, cycloalkyl or alkyl.

In a further preferred embodiment m stands for the number 0, wherein $R^1$ stands for aryl or heteroaryl.

In a preferred embodiment $R^{6a}$ and $R^{6b}$ each stand independently of one another for H; F; Cl; Br; I; methyl; ethyl; n-propyl; isopropyl; n-butyl; sec-butyl; tert-butyl; OH; O-methyl; O-ethyl; O—$(CH_2)_2$—O—$CH_3$; or O—$(CH_2)_2$—OH.

In a further preferred embodiment the radical $R^2$ stands for aryl or heteroaryl, each unsubstituted or mono- or polysubstituted with one or more substituents, each selected independently of one another from the group consisting of F, Cl, Br, I, $NO_2$, CN, OH, O—$C_{1-8}$ alkyl, $OCF_3$, $C_{1-8}$ alkyl, C(=O)—OH, $OF_3$, $NH_2$, NH($C_{1-8}$ alkyl), N($C_{1-8}$ alkyl)$_2$, SH, S—$C_{1-8}$ alkyl, $SCF_3$, $S(=O)_2OH$, benzyl, phenyl, pyridyl and thienyl, wherein benzyl, phenyl, pyridyl, thienyl can each be unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-8}$ alkyl, C(=O)—OH, $OF_3$, $NH_2$, NH($C_{1-8}$ alkyl), N($C_{1-8}$ alkyl)$_2$, SH, S—$C_{1-8}$ alkyl, $SCF_3$, $S(=O)_2OH$.

In a further preferred embodiment the radicals $R^{7a}$, $R^{7b}$, $R^{8a}$, $R^{8b}$, $R^{9a}$ and $R^{9b}$ each stand independently of one another for H; F; Cl; Br; I; $NO_2$; $OF_3$; CN; OH; $OCF_3$; $NH_2$; $C_{1-4}$ alkyl, O—$C_{1-4}$ alkyl, NH—$C_{1-4}$ alkyl, N($C_{1-4}$ alkyl)$_2$, each saturated or unsaturated, branched or unbranched, unsubstituted or mono- or polysubstituted with one or more substituents each selected independently of one another from the group consisting of F, Cl, Br, I, O—$C_{1-4}$ alkyl, OH and $OCF_3$; $C_{3-10}$ cycloalkyl or heterocyclyl, each saturated or unsaturated, unsubstituted or mono- or polysubstituted with one or more substituents each selected independently of one another from the group consisting of F, Cl, Br, I, $C_{1-4}$ alkyl, OH, =O, O—$C_{1-4}$ alkyl, $OCF_3$, $NH_2$, NH—$C_{1-4}$ alkyl and N($C_{1-4}$ alkyl)$_2$.

$R^{7a}$, $R^{7b}$, $R^{8a}$, $R^{8b}$, $R^{9a}$ and $R^{9b}$ preferably each stand independently of one another for H; F; Cl; Br; I; $NO_2$; $CF_3$;

CH$_2$CF$_3$; CN; OH; OCF$_3$, NH$_2$; C$_{1-4}$ alkyl, O—C$_{1-4}$ alkyl, O—C$_{1-4}$ alkyl-OH, O—C$_{1-4}$ alkyl-O—CH$_3$, NH—C$_{1-4}$ alkyl, N(C$_{1-4}$ alkyl)$_2$, each saturated or unsaturated, branched or unbranched, unsubstituted; C$_{3-10}$ cycloalkyl, saturated or unsaturated, unsubstituted or mono- or polysubstituted with one or more substituents each selected independently of one another from the group consisting of F, Cl, Br, I, C$_{1-4}$ alkyl, OH, O—C$_{1-4}$ alkyl.

Particularly preferably, R$^{7a}$, R$^{7b}$, R$^{8a}$, R$^{8b}$, R$^{9a}$ and R$^{9b}$ each stand independently of one another for H; F; Cl; Br; I; NO$_2$; CF$_3$; CN; methyl; ethyl; n-propyl; isopropyl; cyclopropyl; n-butyl; sec-butyl; tert-butyl; CH$_2$CF$_3$; OH; O-methyl; O-ethyl; O—(CH$_2$)$_2$—O—CH$_3$; O—(CH$_2$)$_2$—OH; OCF$_3$; NH$_2$; NH-methyl; N(methyl)$_2$; NH-ethyl; N(ethyl)$_{2i}$ or N(methyl)(ethyl).

Most particularly preferably, R$^{7a}$, R$^{7b}$, R$^{8a}$ and R$^{8b}$ each stand independently of one another for H or methyl.

If R$^{7a}$ forms a cycloalkyl radical with R$^{8a}$, then it is preferably 3- to 6-membered, particularly preferably 6-membered, and can be saturated or unsaturated, unsubstituted or mono- or polysubstituted.

In a further preferred embodiment Y stands for —(CR$^{9a}$R$^{9b}$)—, wherein R$^{9a}$ and R$^{9b}$ stand independently of one another for hydrogen or halogen, particularly preferably R$^{9a}$=R$^{9b}$=hydrogen or halogen, most particularly preferably R$^{9a}$=R$^{9b}$=fluorine or hydrogen.

In a further preferred embodiment the radicals R$^3$, R$^4$ and R$^5$ each stand independently of one another for H; F; Cl; Br; I; NO$_2$; CF$_3$; CN; OH; OCF$_3$; SH; SCF$_3$; NH$_2$; C$_{1-6}$ alkyl, O—C$_{1-6}$ alkyl, O—C(=O)—C$_{1-6}$ alkyl, S—C$_{1-6}$ alkyl, NH(C$_{1-6}$ alkyl), N(C$_{1-6}$ alkyl)$_2$, NH—C(=O)—C$_{1-6}$ alkyl, N(C(=O)—C$_{1-6}$ alkyl)$_2$ or C(=O)—C$_{1-6}$ alkyl, each saturated or unsaturated, branched or unbranched, unsubstituted or mono- or polysubstituted with one or more substituents each selected independently of one another from the group consisting of F, Cl, Br, I, OH and O—C$_{1-4}$ alkyl; C$_{3-7}$ cycloalkyl, saturated or unsaturated, branched or unbranched, unsubstituted or mono- or polysubstituted with one or more substituents each selected independently of one another from the group consisting of F, Cl, Br, I, OH, =O and O—C$_{1-4}$ alkyl; NR$^a$R$^b$, wherein R$^a$ and R$^b$ together with the nitrogen atom linking them form a heterocyclyl, saturated or unsaturated, unsubstituted or mono- or polysubstituted with C$_{1-4}$ alkyl.

The radicals R$^3$, R$^4$ and R$^5$ preferably each stand independently of one another for H; F; Cl; Br; I; NO$_2$; CF$_3$; CN; OH; OCF$_3$; SH; SCF$_3$; methyl; ethyl; n-propyl; isopropyl; butyl; sec-butyl; tert-butyl; CH$_2$CF$_3$; O-methyl; O-ethyl; O-n-propyl; O-isopropyl; O-butyl; O-sec-butyl; O-tert-butyl; O—(CH$_2$)$_2$—O-methyl; O—(CH$_2$)$_2$—OH; O—(C=O)-methyl; O—(C=O)-ethyl; S-methyl; S-ethyl; cyclopropyl; cyclobutyl; NR$^a$R$^b$, wherein R$^a$ and R$^b$ are each selected independently of one another from the group consisting of H, methyl, ethyl, (CH$_2$)$_2$—O-methyl, (CH$_2$)$_2$—OH, (C=O)-methyl, (C=O)-ethyl or R$^a$ and R$^b$ together with the nitrogen atom linking them form a pyrrolidinyl, piperidinyl, 4-methylpiperazinyl or morpholinyl.

The radicals R$^3$, R$^4$ and R$^5$ particularly preferably each stand independently of one another for H; F; Cl; Br; I; methyl; ethyl; n-propyl, isopropyl; cyclopropyl; CN; CF$_3$; O-methyl; OCF$_3$; S-methyl; SCF$_3$.

The radicals R$^3$, R$^3$ and R$^5$ most particularly preferably each stand independently of one another for H; F; Cl; methyl; ethyl; CF$_3$; in particular for H.

Other preferred embodiments of the compounds according to the invention having the general formula (1) have one of the general formulae (2a) or (2b):

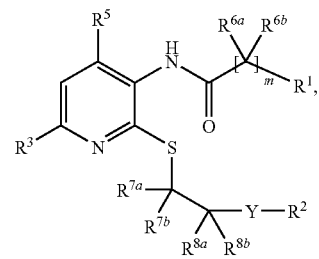

(2a)

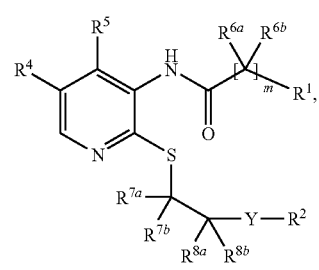

(2b)

Particularly preferred compounds are those from the group comprising:
1 N-[2-[2-(Benzenesulfonyl)-ethylsulfanyl]-pyridin-3-yl]-2-cyclohexyl acetamide;
2 2-Cyclohexyl-N-[2-[2-[[3-(trifluoromethyl)phenyl]sulfonyl]-ethylsulfanyl]-pyridin-3-yl]acetamide;
3 2-Thiophen-2-yl-N-[2-[2-[[3-(trifluoromethyl)phenyl]sulfonyl]-ethylsulfanyl]-pyridin-3-yl]acetamide;
4 N-[2-[2-(Benzenesulfonyl)-ethylsulfanyl]-pyridin-3-yl] benzamide;
5 N-[2-[2-(Benzenesulfonyl)-ethylsulfanyl]-pyridin-3-yl]-3,4-difluorobenzamide;
6 N-[2-[2-(Benzenesulfonyl)-ethylsulfanyl]-pyridin-3-yl]-3-cyclohexyl propionamide;
7 N-[2-[2-(Benzenesulfonyl)-ethylsulfanyl]-pyridin-3-yl]-2-thiophen-2-yl acetamide;
8 N-[2-[2-(Benzenesulfonyl)-ethylsulfanyl]-pyridin-3-yl]-2-(3,5-dimethylphenyl)propionamide;
9 2-(2-Methoxyphenyl)-N-[2-[2-[[3-(trifluoromethyl)phenyl]sulfonyl]-ethylsulfanyl]-pyridin-3-yl]acetamide;
10 2-(4-Methoxyphenyl)-N-[2-[2-[[3-(trifluoromethyl)phenyl]sulfonyl]-ethylsulfanyl]-pyridin-3-yl]acetamide;
11 2-(3-Methoxyphenyl)-N-[2-[2-[[3-(trifluoromethyl)phenyl]sulfonyl]-ethylsulfanyl]-pyridin-3-yl]acetamide
12 2-(2-Hydroxyphenyl)-N-[2-[2-[[3-(trifluoromethyl)phenyl]sulfonyl]-ethylsulfanyl]-pyridin-3-yl]acetamide;
13 2-(4-Hydroxyphenyl)-N-[2-[2-[[3-(trifluoromethyl)phenyl]sulfonyl]-ethylsulfanyl]-pyridin-3-yl]acetamide;
14 2-Cyclopentyl-N-[2-[2-[[3-(trifluoromethyl)phenyl]sulfonyl]-ethylsulfanyl]-pyridin-3-yl]acetamide;
18 N-[2-[2-[[3-(Trifluoromethyl)phenyl]sulfonyl]-ethylsulfanyl]-pyridin-3-yl]-thiophene-2-carboxylic acid amide;
19 N-[2-[2-[[3-(Trifluoromethyl)phenyl]sulfonyl]-ethylsulfanyl]-pyridin-3-yl]-cyclohexane carboxylic acid amide;
20 2-Thiophen-2-yl-N-[2-[2-[[3-(trifluoromethyl)phenyl]sulfanyl]-ethylsulfanyl]-pyridin-3-yl]acetamide;
21 N-[2-(2-Phenylsulfanyl-ethylsulfanyl)-pyridin-3-yl]-2-thiophen-2-yl acetamide;
22 2-Thiophen-2-yl-N-[2-[2-[3-(trifluoromethyl)-phenoxy]-ethylsulfanyl]-pyridin-3-yl]acetamide;
23 2-Thiophen-2-yl-N-[2-[3-[3-(trifluoromethyl)phenyl]-propylsulfanyl]-pyridin-3-yl]acetamide;
24 2-Naphthalen-2-yl-N-[2-[2-[[3-(trifluoromethyl)phenyl]sulfonyl]-ethylsulfanyl]-pyridin-3-yl]acetamide;

25 4-Phenyl-N-[2-[2-[[3-(trifluoromethyl)phenyl]sulfonyl]-ethylsulfanyl]-pyridin-3-yl]-butyramide;
26 3-Thiophen-2-yl-N-[2-[2-[[3-(trifluoromethyl)phenyl]sulfonyl]-ethylsulfanyl]-pyridin-3-yl]propionamide;
27 3-Phenyl-N-[2-[2-[[3-(trifluoromethyl)phenyl]sulfonyl]-ethylsulfanyl]-pyridin-3-yl]propionamide;
28 3-Cyclopentyl-N-[2-[2-[[3-(trifluoromethyl)phenyl]sulfonyl]-ethylsulfanyl]-pyridin-3-yl]propionamide;
29 2-Cyclohexyl-N-[2-[2-[[3-(trifluoromethyl)phenyl]sulfanyl]-ethylsulfanyl]-pyridin-3-yl]acetamide;
31 (E)-3-(4-Fluorophenyl)-N-[2-[2-[[3-(trifluoromethyl)phenyl]sulfonyl]-ethylsulfanyl]-pyridin-3-yl]acrylamide;
33 N-[2-(3-Phenyl-propylsulfanyl)-pyridin-3-yl]-2-thiophen-2-yl acetamide;
35 6-Chloro-N-[2-[2-[[3-(trifluoromethyl)phenyl]sulfonyl]-ethylsulfanyl]-pyridin-3-yl]-pyridine-3-carboxylic acid amide;
36 2-Pyridin-4-yl-N-[2-[2-[[3-(trifluoromethyl)phenyl]sulfonyl]-ethylsulfanyl]-pyridin-3-yl]acetamide;
37 2-(3-Hydroxyphenyl)-N-[2-[2-[[3-(trifluoromethyl)phenyl]sulfonyl]-ethylsulfanyl]-pyridin-3-yl]acetamide;
38 N-[2-[2-[[3-(Trifluoromethyl)phenyl]sulfonyl]-ethylsulfanyl]-pyridin-3-yl]-tetrahydropyrane-3-carboxylic acid amide;
39 2-Tetrahydropyran-2-yl-N-[2-[2-[[3-(trifluoromethyl)phenyl]sulfonyl]-ethylsulfanyl]-pyridin-3-yl]acetamide;
40 2-Tetrahydropyran-4-yl-N-[2-[2-[[3-(trifluoromethyl)phenyl]sulfonyl]-ethylsulfanyl]-pyridin-3-yl]acetamide;
41 3-Cyclohexyl-N-[2-[2-[[3-(trifluoromethyl)phenyl]sulfonyl]-ethylsulfanyl]-pyridin-3-yl]propionamide;
44 2-Cyclohexyl-N-[2-(2-phenylsulfanyl-ethylsulfanyl)-pyridin-3-yl]acetamide;
45 N-[2-(2-Phenoxy-ethylsulfanyl)-pyridin-3-yl]-2-thiophen-2-yl acetamide;
46 2-Pyridin-3-yl-N-[2-[2-[[3-(trifluoromethyl)phenyl]sulfonyl]-ethylsulfanyl]-pyridin-3-yl]acetamide;
47 3-Hydroxy-N-[2-[2-[[3-(trifluoromethyl)phenyl]sulfonyl]-ethylsulfanyl]-pyridin-3-yl]benzamide;
48 N-[2-[2-[[3-(Trifluoromethyl)phenyl]sulfonyl]-ethylsulfanyl]-pyridin-3-yl]-tetrahydropyrane-2-carboxylic acid amide;
49 2-Cycloheptyl-N-[2-[2-[[3-(trifluoromethyl)phenyl]sulfonyl]-ethylsulfanyl]-pyridin-3-yl]acetamide;
50 4-Fluoro-2-methoxy-N-[2-[2-[[3-(trifluoromethyl)phenyl]sulfonyl]-ethylsulfanyl]-pyridin-3-yl]benzamide;
51 4-Fluoro-2-hydroxy-N-[2-[2-[[3-(trifluoromethyl)phenyl]sulfonyl]-ethylsulfanyl]-pyridin-3-yl]benzamide;
52 2-(1,2,3,4-Tetrahydronaphthalen-2-yl)-N-[2-[2-[[3-(trifluoromethyl)phenyl]sulfonyl]-ethylsulfanyl]-pyridin-3-yl]acetamide;
53 2-Hydroxy-N-[2-[2-[[3-(trifluoromethyl)phenyl]sulfonyl]-ethylsulfanyl]-pyridin-3-yl]benzamide;
55 2-(3-Oxocyclohexyl)-N-[2-[2-[[3-(trifluoromethyl)phenyl]sulfonyl]-ethylsulfanyl]-pyridin-3-yl]acetamide;
56 N-[4-Methyl-2-[2-[[3-(trifluoromethyl)phenyl]sulfonyl]-ethylsulfanyl]-pyridin-3-yl]-2-thiophen-2-yl acetamide;
57 3-(1,2,3,4-Tetrahydronaphthalen-2-yl)-N-[2-[2-[[3-(trifluoromethyl)phenyl]sulfonyl]-ethylsulfanyl]-pyridin-3-yl]propionamide;
58 3-Cycloheptyl-N-[2-[2-[[3-(trifluoromethyl)phenyl]sulfonyl]-ethylsulfanyl]-pyridin-3-yl]propionamide;
59 2-(Benzo[b]thiophen-2-yl)-N-[2-[2-[[3-(trifluoromethyl)phenyl]sulfonyl]-ethylsulfanyl]-pyridin-3-yl]acetamide;
60 2-Pyridin-2-yl-N-[2-[2-[[3-(trifluoromethyl)phenyl]sulfonyl]-ethylsulfanyl]-pyridin-3-yl]acetamide
61 N-[2-[2-[(4-Fluorophenyl)sulfanyl]-ethylsulfanyl]-pyridin-3-yl]-3,3-dimethyl butyramide;
62 2-(5-Bicyclo[2.2.1]heptanyl)-N-[2-[2-[[3-(trifluoromethyl)phenyl]sulfonyl]-ethylsulfanyl]-pyridin-3-yl]acetamide;
63 N-[2-[2-(4-Fluorophenoxy)-ethylsulfanyl]-pyridin-3-yl]-3,3-dimethyl butyramide;
64 3,4-Difluoro-N-[2-[2-(4-fluorophenoxy)-ethylsulfanyl]-pyridin-3-yl]benzamide;
65 3,4-Difluoro-N-[2-[3-(4-fluorophenyl)-propylsulfanyl]-pyridin-3-yl]benzamide;
66 N-[2-[3-(4-Fluorophenyl)-propylsulfanyl]-pyridin-3-yl]-3,3-dimethyl butyramide;
67 2-Cycloheptyl-N-[2-[2-[(4-fluorophenyl)sulfonyl]-ethylsulfanyl]-pyridin-3-yl]acetamide;
68 2-Cyclohexyl-2,2-difluoro-N-[2-[2-[[3-(trifluoromethyl)phenyl]sulfonyl]-ethylsulfanyl]-pyridin-3-yl]acetamide;
or the physiologically compatible salts thereof.

The substituted N-(2-mercaptopyridin-3-yl)amides according to the invention and the corresponding acids, bases, salts and solvates are suitable as pharmaceutical active ingredients in medicaments.

The invention therefore also provides a medicament containing at least one substituted N-(2-mercaptopyridin-3-yl) amide according to the invention having the general formula (1), wherein the radicals $R^1$ to $R^5$ have the meaning given above, and optionally one or more pharmaceutically compatible auxiliary substances.

The medicaments according to the invention optionally contain, in addition to at least one compound according to the invention, suitable additives and/or auxiliary substances, including carrier materials, fillers, solvents, diluents, dyes and/or binders, and can be administered as liquid dosage forms in the form of injection solutions, drops or juices, as semi-solid dosage forms in the form of granules, tablets, pellets, patches, capsules, plasters/spray plasters or aerosols. The choice of auxiliary substances, etc., and the amount thereof to use depend on whether the medicament is to be administered by oral, peroral, parenteral, intravenous, intraperitoneal, intradermal, intramuscular, intranasal, buccal, rectal or local means, for example on the skin, mucous membranes or in the eyes. Preparations in the form of tablets, pastilles, capsules, granules, drops, juices and syrups are suitable for oral administration; solutions, suspensions, easily reconstitutable dry preparations and sprays are suitable for parenteral, topical and inhalative administration. Compounds according to the invention in a depot formulation, in dissolved form or in a plaster, optionally with addition of agents promoting skin penetration, are suitable preparations for percutaneous administration. Preparation forms suitable for oral or percutaneous administration can deliver the compounds according to the invention on a delayed release basis. The compounds according to the invention can also be used in parenteral long-term depot forms, such as implants or implanted pumps, for example. Other additional active ingredients known to the person skilled in the art can be added in principle to the medicaments according to the invention.

These medicaments according to the invention are suitable for influencing KCNQ2/3 channels and exert an agonistic or antagonistic, in particular an agonistic, action.

The medicaments according to the invention are preferably suitable for the treatment of disorders or diseases which are at least partly mediated by KCNQ2/3 channels.

The medicaments according to the invention are preferably suitable for the treatment of one or more diseases chosen from the group consisting of pain, preferably pain chosen from the group consisting of acute pain, chronic pain, neuropathic pain, muscular pain and inflammatory pain, epilepsy, urinary incontinence, anxiety states, dependency, mania, bipolar disorders, migraine, cognitive diseases, dystonia-associated dyskinesias and/or urinary incontinence.

The medicaments according to the invention are particularly preferably suitable for the treatment of pain, most particularly preferably chronic pain, neuropathic pain, inflammatory pain and muscular pain.

The medicaments according to the invention are further particularly preferably suitable for the treatment of epilepsy.

The invention also provides the use of at least one substituted 2-mercapto-3-aminopyridine according to the invention and optionally one or more pharmaceutically compatible auxiliary substances for the preparation of a medicament for the treatment of disorders or diseases which are at least partly mediated by KCNQ2/3 channels.

Preference is given to the use of at least one substituted 2-mercapto-3-aminopyridine according to the invention and optionally one or more pharmaceutically compatible auxiliary substances for the preparation of a medicament for the treatment of pain, preferably pain chosen from the group consisting of acute pain, chronic pain, neuropathic pain, muscular pain and inflammatory pain; epilepsy, urinary incontinence, anxiety states, dependency, mania, bipolar disorders, migraine, cognitive diseases, dystonia-associated dyskinesias and/or urinary incontinence.

Particularly preferred is the use of at least one substituted 2-mercapto-3-aminopyridine according to the invention and optionally one or more pharmaceutically compatible auxiliary substances for the preparation of a medicament for the treatment of pain, most particularly preferably chronic pain, neuropathic pain, inflammatory pain and muscular pain.

Also particularly preferred is the use of at least one substituted 2-mercapto-3-aminopyridine according to the invention and optionally one or more pharmaceutically compatible auxiliary substances for the preparation of a medicament for the treatment of epilepsy.

The invention also provides at least one substituted 2-mercapto-3-aminopyridine according to the invention and optionally one or more pharmaceutically compatible auxiliary substances for the treatment of disorders or diseases which are at least partly mediated by KCNQ2/3 channels.

The invention also provides at least one substituted 2-mercapto-3-aminopyridine according to the invention and optionally one or more pharmaceutically compatible auxiliary substances for the treatment of pain, preferably pain chosen from the group consisting of acute pain, chronic pain, neuropathic pain, muscular pain and inflammatory pain; epilepsy, urinary incontinence, anxiety states, dependency, mania, bipolar disorders, migraine, cognitive diseases, dystonia-associated dyskinesias and/or urinary incontinence.

Particularly preferred is at least one substituted 2-mercapto-3-aminopyridine according to the invention and optionally one or more pharmaceutically compatible auxiliary substances for the treatment of pain, most particularly preferably chronic pain, neuropathic pain, inflammatory pain and muscular pain.

Particularly preferred is also at least one substituted 2-mercapto-3-aminopyridine according to the invention and optionally one or more pharmaceutically compatible auxiliary substances for the treatment of epilepsy.

The effectiveness against pain can be demonstrated for example in the Bennett or Chung model (Bennett, G. J. and Xie, Y. K., A peripheral mononeuropathy in rat that produces disorders of pain sensation like those seen in man, Pain 1988, 33 (1), 87-107; Kim, S. H. and Chung, J. M., An experimental model for peripheral neuropathy produced by segmental spinal nerve ligation in the rat, Pain 1992, 50 (3), 355-363). The effectiveness against epilepsy can be demonstrated for example in the DBA/2 mouse model (De Sarro et al., Naunyn-Schmiedeberg's Arch. Pharmacol. 2001, 363, 330-336).

The substituted N-(2-mercaptopyridin-3-yl)amides according to the invention preferably have an $EC_{50}$ value of at most 10 µM or at most 6 µM, more preferably at most 5 µM or at most 4 µM, even more preferably at most 3 µM or at most 2 µM, most preferably at most 1 µM or at most 0.7 µM and in particular at most 0.6 µM or at most 0.4 µM. Methods for determining the $EC_{50}$ value are known to the person skilled in the art. The $EC_{50}$ value is preferably determined by fluorimetry, particularly preferably by the method described in "Pharmacological experiments".

The invention also provides methods for preparing the substituted N-(2-mercaptopyridin-3-yl)amides according to the invention.

The chemicals and reaction components used in the reactions described below are available commercially or can be produced by conventional methods known to the person skilled in the art.

General Reaction Scheme

Scheme 1:

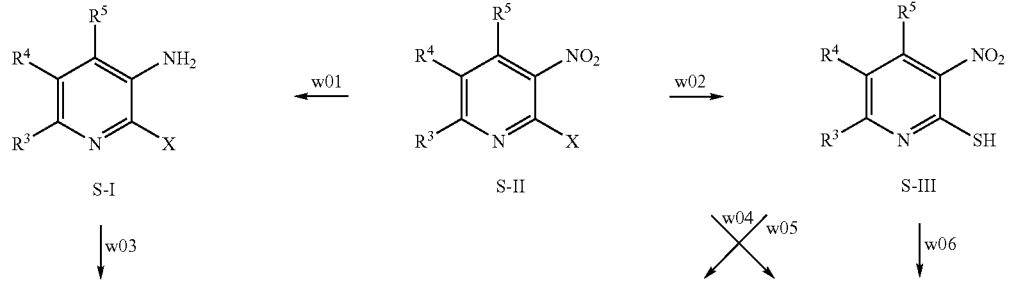

-continued

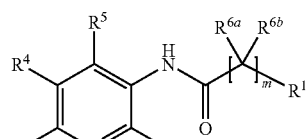

S-IV

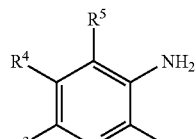

S-V

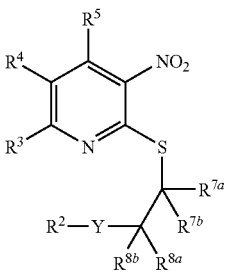

S-VI

↓w07  ✗w08/w09  ↘w10

↓w11

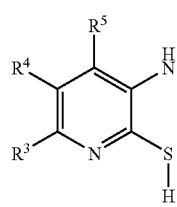

S-VII

→w12→

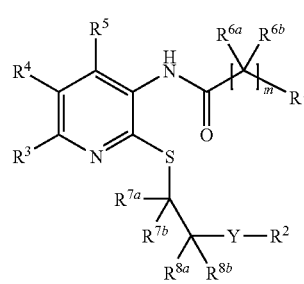

(I)

←w13←

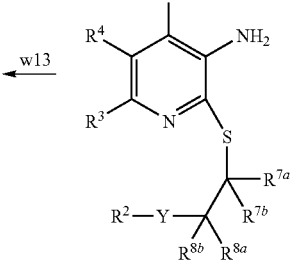

S-VIII

In steps w01, w05 and w11 the nitro groups of compounds S-II and S-VI can be converted into the corresponding amines S-I, S-V and S-VIII by means of reduction methods familiar to the person skilled in the art, such as for example in the presence of metals in acid solution or by catalytic hydrogenation.

In steps w02 and w07 the 2-halogen pyridines S-II and S-IV, in which X stands for halogen, preferably for F or chlorine, are firstly converted into the corresponding thio ethers by means of methods known to the person skilled in the art, such as for example by substitution with a thiol, for example 3-mercaptopropanoic acid methyl ester, and then cleaved to the thiol S-III or S-VII, optionally in the presence of an acid or a base.

In steps w03, w09 and w13 the amines S-I, S-V and S-VIII are converted into the corresponding amides S-IV, S-VII and I. This can be achieved for example by reaction with an acid chloride $R^1$—C(=O)—Cl by means of methods familiar to the person skilled in the art, optionally in the presence of a base or by reaction with an acid $R^1$—C(=O)—OH in the presence of a suitable coupling reagent, for example HATU or CDI, optionally with addition of a base.

In steps w04 and w08 the thio ethers I and S-VI are formed starting from the 2-halogen pyridines S-II and S-IV, in which X stands for halogen, preferably for fluorine or chlorine, by means of methods familiar to the person skilled in the art, for example by reaction with the corresponding thiol $R^2$—SH in an ipso-substitution, optionally in the presence of a base.

In steps w06, w10 and w12 the thiols S-III, S-V and S-VII can be converted into the corresponding thio ethers S-VI, S-VIII and I by means of methods familiar to the person skilled in the art, for example by reaction with an alkyl halide $R^2$-Hal, optionally in the presence of a base.

The methods familiar to the person skilled in the art for performing reaction steps w01 to w13 can be found in the standard works on organic chemistry, such as for example J. March, Advanced Organic Chemistry, Wiley & Sons, 6th edition, 2007; F. A. Carey, R. J. Sundberg, Advanced Organic Chemistry, Parts A and B, Springer, 5th edition, 2007); various authors, Compendium of Organic Synthetic Methods, Wiley & Sons. In addition, further methods and references to the literature can be obtained from the standard databases such as for example the Reaxys® database from Elsevier, Amsterdam, NL or the SciFinder® database of the American Chemical Society, Washington, US.

DESCRIPTION OF THE SYNTHESES

Abbreviations

AcOH acetic acid
aq. aqueous
d days
BOP 1-benzotriazolyloxy-tris-(dimethylamino)-phosphonium hexafluorophosphate
brine saturated sodium chloride solution
DCC N,N'-dicyclohexyl carbodiimide
DCM dichloromethane
DIPEA N,N-diisopropylethylamine
DMF N,N-dimethyl formamide
DMAP 4-dimethylaminopyridine
EDC N-(3-dimethylaminopropyl)-N'-ethyl carbodiimide
EE ethyl acetate
ether diethyl ether
EtOH ethanol
sat. saturated
h hour(s)
HATU O-(7-azabenzotriazol-1-yl)-N,N,N',N'-tetramethyluronium hexafluorophosphate
HBTU O-(benzotriazol-1-yl)-N,N,N',N'-tetramethyluronium hexafluorophosphate HOAt 1-hydroxy-7-azabenzotriazole
sol. solution
LG leaving group
m/z mass-to-charge ratio
MeCN acetonitrile
MeOH methanol
min minutes
MS mass spectrometry
N/A not available
NEt$_3$ triethylamine
RG retigabine
RT room temperature 23±7° C.
SC column chromatography on silica gel
THF tetrahydrofuran
vv ratio by volume All starting materials not explicitly described were either available commercially (suppliers can be found for example in the Symyx® Available Chemicals Database from MDL, San Ramon, US), or their synthesis is already accurately described in the specialist literature (experimental procedures can be found for example in the Reaxys® database from Elsevier, Amsterdam, NL), or can be prepared by methods known to the person skilled in the art.

Silica gel 60 (0.040-0.063 mm) was used as the stationary phase for column chromatography (SC).

The analytical characterisation of all intermediates and example compounds was performed by means of $^1$H-NMR spectroscopy. Analyses by mass spectrometry (MS, m/z stated for [M+H]$^+$) were also performed for all example compounds and selected intermediates.

Synthesis of Intermediates

Synthesis of intermediate VPF-001: [2-[2-[[3-(Trifluoromethyl)-phenyl]sulfonyl]-ethylsulfanyl]-pyridin-3-yl]amine a) Synthesis of 3-nitro-2-[2-[[3-(trifluoromethyl) phenyl]sulfonyl]-ethylsulfanyl]pyridine 4.15 g (30.0 mmol) potassium carbonate and 2.59 g (9.5 mmol) (1-(3-chloroethylsulfonyl)-3-(trifluoromethyl)benzene were added to a solution of 1.56 g (10.0 mmol) 3-nitro-2-mercaptopyridine in acetone (50 ml) at room temperature and then heated for 16 h at 60° C. Then the mixture was concentrated to small volume under vacuum and the residue was taken up with water and EE. The phases were separated and the organic phase was washed with water and brine, dried over Na$_2$SO$_4$, filtered and concentrated to small volume under vacuum. The crude product was washed repeatedly with hexane to produce 2.35 g (6.0 mmol, 63%) 3-nitro-2-[2-[[3-(trifluoromethyl)phenyl]sulfonyl]-ethylsulfanyl]pyridine.

b) Synthesis of [2-[2-[[3-(trifluoromethyl)-phenyl] sulfonyl]-ethylsulfanyl]-pyridin-3-yl]amine 1.31 g (20 mmol) zinc was added to a solution of 1.96 g (5.0 mmol) 3-nitro-2-[2-[[3-(trifluoromethyl)phenyl]sulfonyl] ethyl-sulfanyl]pyridine in ethanol (45 ml) and the mixture was cooled to 0° C. 200 ml (0.2 M, 40 mmol) of an aqueous NH$_4$Cl solution were added at this temperature and then the mixture was heated for 30 min at 90° C. Then the mixture was concentrated to small volume under vacuum and the residue was taken up with water and neutralised with NaHCO$_3$. It was then extracted with EE and the organic phase was dried over Na$_2$SO$_4$, filtered and concentrated to small volume under vacuum. Column chromatography (hexane/EE 4:1) of the residue yielded 1.38 g (3.8 mmol, 76%) [2-[2-[[3-(trifluoromethyl)-phenyl]sulfonyl]-ethylsulfanyl]-pyridin-3-yl] amine.

Synthesis of intermediate VPF-002: [2-[2-(Benzenesulfonyl)-ethylsulfanyl]-pyridin-3-yl]amine a) Synthesis of 2-[2-(benzenesulfonyl)-ethylsulfanyl]-3-nitropyridine 1.8 g (16.0 mmol) potassium tert-butylate were added to a solution of 3.0 g (14.8 mmol) 2-(phenylsulfonyl)ethanethiol in DMF (35 ml) and the mixture was stirred for 30 min at room temperature. Then 2.5 g (15.8 mmol) 2-chloro-3-nitropyridine were added and the mixture was stirred for a further 1 h at RT. Then it was diluted with a brine/EE mixture (1:1 vv) and stirred for a further 30 min at RT. Then the organic phase was separated off, washed with water and brine, dried over Na$_2$SO$_4$, filtered and concentrated to small volume under vacuum. Column chromatography (hexane/EE 6:1) of the residue yielded 2.2 g (6.8 mmol, 46%) 2-[2-(benzenesulfonyl)-ethylsulfanyl]-3-nitropyridine.

b) Synthesis of 2-[2-(benzenesulfonyl)-ethylsulfanyl]-pyridin-3-yl]amine 5.5 ml of concentrated aqueous hydrochloric acid and 1.1 g (19.7 mmol) of iron chips were added to a solution of 2.2 g (6.8 mmol) 2-[2-(benzenesulfonyl)-ethylsulfanyl]-3-nitropyridine in MeOH (34 ml) and then heated for 45 min at 60° C. Then the mixture was diluted with MeOH, filtered through kieselguhr and the filtrate concentrated to small volume under vacuum. The residue was taken up with water and extracted with EE. The organic phase was washed with water and brine, dried over Na$_2$SO$_4$, filtered and concentrated to small volume under vacuum. Column chromatography (hexane/EE 3:1) of the residue yielded 1.5 g (5.1 mmol, 75%) 2-[2-(benzenesulfonyl)-ethylsulfanyl]-pyridin-3-yl]amine.

Synthesis of intermediate VPF-006: [2-(2-Phenylsulfanyl-ethylsulfanyl)-pyridin-3-yl]amine a) Synthesis of 3-nitro-2-(2-phenylsulfanyl-ethylsulfanyl)pyridine 3.44 g (20.0 mmol) (2-chloroethyl)(phenyl)sulfane and 5.53 g (40.0 mmol) potassium carbonate were added to a solution of 1.56 g (10.0 mmol) 2-mercapto-3-nitropyridine in DMF (30 ml) and heated for 4 h at 60° C. Then the mixture was diluted with EE and washed with brine. The organic phase was separated off, dried over Na$_2$SO$_4$, filtered and concentrated to small volume under vacuum. Column chromatography (hexane/EE 9:1) of the residue yielded 1.93 g (6.6 mmol, 66%) 3-nitro-2-(2-phenylsulfanyl-ethylsulfanyl) pyridine.

b) Synthesis of [2-(2-phenylsulfanyl-ethylsulfanyl)-pyridin-3-yl]amine

Starting from 1.46 g (5.0 mmol) 3-nitro-2-(2-phenylsulfanyl-ethylsulfanyl)pyridine and using the method described for precursor VPF-001 step b), 878 mg (3.4 mmol, 67%) [2-(2-phenylsulfanyl-ethylsulfanyl)-pyridin-3-yl]amine were obtained.

Synthesis of Further Intermediates

The synthesis of further intermediates took place by the methods already described. Table 1 shows which compound was prepared by which method. The starting materials and reagents used in each case are apparent to the person skilled in the art.

TABLE 1

| Inter-mediate | Chemical name | Preparation analogous to intermediate | Yield [%] |
|---|---|---|---|
| VPF-007 | [2-[2-[[3-(Trifluoromethyl)phenyl]sulfanyl]-ethylsulfanyl]-pyridin-3-yl] amine | VPF-006 | 38 (2 stages) |
| VPF-008 | [2-(3-Phenyl-propylsulfanyl)-pyridin-3-yl] amine | VPF-006 | 34 (2 stages) |
| VPF-009 | [2-[3-[3-(Trifluoromethyl)phenyl]-propylsulfanyl]-pyridin-3-yl] amine | VPF-006 | 46 (2 stages) |
| VPF-010 | [2-(2-Phenoxy-ethylsulfanyl)-pyridin-3-yl] amine | VPF-006 | 47 (2 stages) |
| VPF-011 | [2-[2-[3-(Trifluoromethyl)-phenoxy]-ethylsulfanyl]-pyridin-3-yl] amine | VPF-006 | 44 (2 stages) |
| VPF-012 | [4-Methyl-2-[2-[[3-(trifluoromethyl)-phenyl]sulfonyl]-ethylsulfanyl]-pyridin-3-yl] amine | VPF-001 | 44 (2 stages) |
| VPF-013 | [2-[2-[(4-Fluorophenyl)sulfanyl]-ethylsulfanyl]-pyridin-3-yl] amine | VPF-001 | 20 (2 stages) |
| VPF-014 | [2-[2-(4-Fluorophenoxy)-ethylsulfanyl]-pyridin-3-yl] amine | VPF-006 | 56 (2 stages) |
| VPF-015 | [2-[3-(4-Fluorophenyl)-propylsulfanyl]-pyridin-3-yl] amine | VPF-006 | 48 (2 stages) |
| VPF-016 | [2-[2-[(4-Fluorophenyl)sulfonyl]-ethylsulfanyl]-pyridin-3-yl] amine | VPF-001 | 53 (2 stages) |

Synthesis of the Example Compounds

Synthesis of example compound 1: N-[2-[2-(Benzenesulfonyl)-ethylsulfanyl]-pyridin-3-yl]-2-cyclohexyl acetamide 336 mg (4.0 mmol) NaHCO$_3$ were added to a solution of 294 mg (1.0 mmol) [2-[2-(benzenesulfonyl)-ethylsulfanyl]-pyridin-3-yl]amine (VPF-002) in dioxane (10 ml) and the mixture was stirred for 10 min at RT. Then 321 mg (2.0 mmol) 2-cyclohexylacetylchloride were added at 5° C. and the mixture was stirred for a further 16 h at RT. Then it was diluted with EE and filtered through kieselguhr. The filtrate was washed with a saturated aqueous NaHCO$_3$ solution, water and brine, dried over Na$_2$SO$_4$, filtered and concentrated to small volume under vacuum. Column chromatography (hexane/EE 6:1) of the residue yielded 368 mg (0.9 mmol, 88%) N-[2-[2-(benzenesulfonyl)-ethyl-sulfanyl]-pyridin-3-yl]-2-cyclohexyl acetamide. MS: m/z 419.1 [M+H]$^+$.

Synthesis of example compound 9: 2-(2-Methoxyphenyl)-N-[2-[2-[[3-(trifluoromethyl)phenyl]sulfonyl]-ethylsulfanyl]-pyridin-3-yl]acetamide 1.7 g (4.0 mmol) HATU and 1.36 ml (8.0 mmol) DIPEA were added to a solution of 582 mg (3.5 mmol) 2-(2-methoxyphenyl)acetic acid in DCM (10 ml) and the mixture was cooled to 0° C. After stirring for 15 min a solution of 725 mg (2.0 mmol) [2-[2-[[3-(trifluoromethyl)phenyl]sulfonyl]-ethylsulfanyl]-pyridin-3-yl]amine (VPF-001) in DCM (6 ml) was added at 0° C. The mixture was then stirred for 16 h at room temperature. Then it was diluted with DCM and washed successively with a saturated aqueous NH$_4$Cl solution, a saturated aqueous NaHCO$_3$ solution and brine. The organic phase was dried over Na$_2$SO$_4$, filtered and concentrated to small volume under vacuum. Column chromatography (hexane/EE 7:3) of the residue yielded 827 mg (1.6 mmol, 81%) 2-(2-methoxyphenyl)-N-[2-[2-[[3-(trifluoromethyl)-phenyl]sulfonyl]-ethylsulfanyl]-pyridin-3-yl]acetamide. MS: m/z 511.1 [M+H]$^+$.

Synthesis of example compound 12: 2-(2-Hydroxyphenyl)-N-[2-[2-[[3-(trifluoromethyl)phenyl]sulfonyl]-ethylsulfanyl]-pyridin-3-yl]acetamide 214 µl (2.5 mmol) BBr$_3$ were added to a solution of 511 mg (1.0 mmol) 2-(2-methoxyphenyl)-N-[2-[2-[[3-(trifluoromethyl)-phenyl]sulfonyl]-ethylsulfanyl]-pyridin-3-yl]acetamide (example compound 9) in DCM (9 ml) at 10° C. and the mixture was stirred for 2 h at this temperature.

Then it was quenched with water and extracted with DCM. The organic phase was washed with a saturated aqueous NaHCO$_3$ solution and brine, dried over Na$_2$SO$_4$, filtered and concentrated to small volume under vacuum. Column chromatography (hexane/EE 3:2) of the residue yielded 338 mg (0.7 mmol, 68%) 2-(2-hydroxyphenyl)-N-[2-[2-[[3-(trifluoromethyl)-phenyl]sulfonyl]-ethylsulfanyl]-pyridin-3-yl]acetamide. MS: m/z 497.1 [M+H]$^+$.

Synthesis of example compound 14: 2-Cyclopentyl-N-[2-[2-[[3-(trifluoromethyl)phenyl]sulfonyl]-ethylsulfanyl]-pyridin-3-yl]acetamide 254 µl (3.0 mmol) oxalylchloride were added to a solution of 192 mg (1.5 mmol) 2-cyclopentyl acetic acid in DCM (10 ml) and the mixture was stirred for 3 h at RT. Then the mixture was concentrated to small volume under vacuum and the residue was taken up with dioxane (6 ml). This solution was added at 0° C. to a solution of 362 mg (1.0 mmol) [2-[2-[[3-(trifluoromethyl)phenyl]sulfonyl]-ethylsulfanyl]-pyridin-3-yl]amine (VPF-001) in dioxane (5 ml). Then the reaction solution was mixed with 420 mg (5.0 mmol) NaHCO$_3$ and stirred for 16 h at RT. Then the mixture was concentrated to small volume under vacuum and the residue was taken up with water. Then it was extracted with EE and the organic phase was washed with a saturated aqueous NaHCO$_3$ solution and brine, dried over Na$_2$SO$_4$, filtered and concentrated to small volume under vacuum. Column chromatography (hexane/EE 3:1) of the residue yielded 231 mg (0.5 mmol, 54%) 2-cyclopentyl-N-[2-[2-[[3-(trifluoromethyl)-phenyl]sulfonyl]-ethylsulfanyl]-pyridin-3-yl]acetamide. MS: m/z 473.1 [M+H]$^+$.

Synthesis of example compound 21: N-[2-[2-(2-Phenylsulfanyl-ethylsulfanyl)-pyridin-3-yl]-2-thiophen-2-yl acetamide 420 mg (5.0 mmol) NaHCO$_3$ and 402 mg (2.5 mmol) 2-(thiophen-2-yl)acetic acid chloride were added to a solution of 262 mg (1.0 mmol) [2-(2-phenylsulfanyl-ethylsulfanyl)-pyridin-3-yl]amine (VPF-006) in dioxane (25 ml) at 0° C. and then the mixture was stirred for 16 h at RT. Then it was diluted with EE and washed with water and brine. The organic phase was dried over Na$_2$SO$_4$, filtered and concentrated to small volume under vacuum. Column chromatography (hexane/EE 9:1) of the residue yielded 186 mg (0.5 mmol, 48%) N-[2-(2-phenylsulfanyl-ethylsulfanyl)-pyridin-3-yl]-2-thiophen-2-yl acetamide. MS: m/z 387.1 [M+H]$^+$.

Synthesis of example compound 50: 4-Fluoro-2-methoxy-N-[2-[2-[[3-(trifluoromethyl)phenyl]sulfonyl]-ethylsulfanyl]-pyridin-3-yl]benzamide A solution of 510 mg (3.0 mmol) 4-fluoro-2-methoxybenzoic acid in thionyl chloride (3 ml) was stirred for 2 h at RT.

Then the mixture was concentrated to small volume under vacuum and the residue was taken up with dioxane (15 ml). Then a solution of 1.09 g (3.0 mmol) [2-[2-[[3-(trifluoromethyl)phenyl]sulfonyl]-ethylsulfanyl]-pyridin-3-yl]amine (VPF-001) in dioxane (15 ml) and 1.06 g (10.0 mmol) Na$_2$CO$_3$ were added and the mixture was stirred for 16 h at RT. Then the mixture was concentrated to small volume under vacuum and the residue was taken up with water and extracted with EE. The organic phase was washed with a saturated aqueous NaHCO$_3$ solution and brine, dried over Na$_2$SO$_4$, filtered and concentrated to small volume under vacuum. Crystallisation (DCM/hexane) of the residue yielded 895 mg (1.7 mmol, 58%) 4-fluoro-2-methoxy-N-[2-[2-[[3-(trifluoromethyl)-phenyl]sulfonyl]-ethylsulfanyl]-pyridin-3-yl]-benzamide. MS: m/z 514.1 [M+H]$^+$.

Synthesis of example compound 51: 4-Fluoro-2-hydroxy-N-[2-[2-[[3-(trifluoromethyl)phenyl]sulfonyl]-ethylsulfanyl]-pyridin-3-yl]benzamide A solution of 515 mg (1.0 mmol) 4-fluoro-2-methoxy-N-[2-[2-[[3-(trifluoromethyl)phenyl]sulfonyl]-ethylsulfanyl]-pyridin-3-yl]benzamide (example compound 50) in DCM (5 ml) was cooled to −78° C. 5 ml (1 M in DCM, 5.0 mmol) BBr$_3$ were added at this temperature and the mixture was stirred for 1 h at −78° C. Then the reaction solution was poured into an iced water mixture and it was adjusted to pH 8 with NaHCO$_3$. Then it was extracted with DCM and the organic phase was washed with water and brine, dried over Na$_2$SO$_4$, filtered and concentrated to small volume under vacuum. 290 mg of 4-fluoro-2-hydroxy-N-[2-[2-[[3-(trifluoromethyl)phenyl]sulfonyl]-ethylsulfanyl]-pyridin-3-yl]benzamide were obtained as residue. MS: m/z 501.0 [M+H]$^+$.

Synthesis of example compound 55: 2-(3-Oxocyclohexyl)-N-[2-[2-[[3-(trifluoromethyl)phenyl]sulfonyl]-ethylsulfanyl]-pyridin-3-yl]acetamide 560 µl (4.23 mmol) 1-chloro-N,N,2-trimethylprop-1-en-1-amine were added at 0° C. to a solution of 550 mg (35.2 mmol) 2-(3-oxocyclohexyl)acetic acid in DCM (7 ml). After stirring for 15 min at 0° C., 1.5 g (4.23 mmol) [2-[2-[[3-(trifluoromethyl)phenyl]sulfonyl]-ethylsulfanyl]-pyridin-3-yl]amine (VPF-001) were added. Then the reaction solution was stirred for a further 16 h at 0° C. It was then diluted with water (30 ml) and extracted with DCM (3×50 ml). The combined organic phases were washed with water and brine, dried over Na$_2$SO$_4$, filtered and concentrated to small volume under vacuum. Column chromatography (hexane/EE 6:4) of the residue yielded 220 mg (0.44 mmol, 13%) 2-(3-oxocyclohexyl)-N-[2-[2-[[3-(trifluoromethyl)phenyl]sulfonyl]-ethylsulfanyl]-pyridin-3-yl]acetamide. MS: m/z 501.1 [M+H]$^+$.

Synthesis of example compound 60: 2-Pyridin-2-yl-N-[2-[2-[[3-(trifluoromethyl)phenyl]sulfonyl]-ethylsulfanyl]-pyridin-3-yl]acetamide 302 mg (2.0 mmol) methyl 2-(pyridin-2-yl)acetate were added to a solution of 362 mg (1.0 mmol) [2-[2-[[3-(trifluoromethyl)phenyl]sulfonyl]-ethylsulfanyl]-pyridin-3-yl]amine (VPF-001) in xylene (4 ml) and the mixture was then heated for 7 h at 150° C. After cooling to RT the mixture was diluted with EtOAc and the phases were separated. The organic phase was washed with water and brine, dried over Na$_2$SO$_4$, filtered and concentrated to small volume under vacuum. Column chromatography (hexane/EE 6:4) of the residue yielded 154 mg (0.32 mmol, 32%) 2-pyridin-2-yl-N-[2-[2-[[3-(trifluoromethyl)phenyl]sulfonyl]-ethylsulfanyl]-pyridin-3-yl]acetamide. MS: m/z 482.1 [M+H]$^+$.

Synthesis of Further Example Compounds

The synthesis of further example compounds took place by the methods already described. Table 2 shows which compound was prepared by which method. The starting materials and reagents used in each case are apparent to the person skilled in the art.

TABLE 2

| Example | Chemical name | Preparation analogous to example | Yield [%] | MS m/z [M+H]$^+$ |
|---|---|---|---|---|
| 2 | 2-Cyclohexyl-N-[2-[2-[[3-(trifluoromethyl)phenyl]sulfonyl]-ethylsulfanyl]-pyridin-3-yl] acetamide | 1 | 89 | 487.1 |
| 3 | 2-Thiophen-2-yl-N-[2-[2-[[3-(trifluoromethyl)phenyl]sulfonyl]-ethylsulfanyl]-pyridin-3-yl] acetamide | 1 | 57 | 487 |
| 4 | N-[2-[2-(Benzenesulfonyl)-ethylsulfanyl]-pyridin-3-yl] benzamide | 1 | 92 | 399.1 |
| 5 | N-[2-[2-(Benzenesulfonyl)-ethylsulfanyl]-pyridin-3-yl]-3,4-difluorobenzamide | 1 | 53 | 435.1 |
| 6 | N-[2-[2-(Benzenesulfonyl)-ethylsulfanyl]-pyridin-3-yl]-3-cyclohexyl propionamide | 1 | 50 | 433.2 |
| 7 | N-[2-[2-(Benzenesulfonyl)-ethylsulfanyl]-pyridin-3-yl]-2-thiophen-2-yl acetamide | 1 | 56 | 419 |
| 8 | N-[2-[2-(Benzenesulfonyl)-ethylsulfanyl]-pyridin-3-yl]-2-(3,5-dimethylphenyl) propionamide | 1 | 42 | 455.1 |
| 10 | 2-(4-Methoxyphenyl)-N-[2-[2-[[3-(trifluoromethyl)phenyl]sulfonyl]-ethylsulfanyl]-pyridin-3-yl] acetamide | 9 | 83 | 511.1 |
| 11 | 2-(3-Methoxyphenyl)-N-[2-[2-[[3-(trifluoromethyl)-phenyl]sulfonyl]-ethylsulfanyl]-pyridin-3-yl] acetamide | 9 | 71 | 511.1 |
| 13 | 2-(4-Hydroxyphenyl)-N-[2-[2-[[3-(trifluoromethyl)phenyl]sulfonyl]-ethylsulfanyl]-pyridin-3-yl] acetamide | 12 | 56 | 497.1 |

TABLE 2-continued

| Example | Chemical name | Preparation analogous to example | Yield [%] | MS m/z [M+H]+ |
|---|---|---|---|---|
| 18 | N-[2-[2-[[3-(Trifluoromethyl)phenyl]sulfonyl]-ethylsulfanyl-pyridin-3-yl]-thiophene-2-carboxylic acid amide | 14 | 58 | 473 |
| 19 | N-[2-[2-[[3-(Trifluoromethyl)phenyl]sulfonyl]-ethylsulfanyl]-pyridin-3-yl]-cyclohexane carboxylic acid amide | 14 | 60 | 473.1 |
| 20 | 2-Thiophen-2-yl-N-[2-[2-[[3-(trifluoromethyl)phenyl]sulfanyl]-ethylsulfanyl]-pyridin-3-yl] acetamide | 21 | 72 | 455 |
| 22 | 2-Thiophen-2-yl-N-[2-[2-[3-(trifluoromethyl)-phenoxy]-ethylsulfanyl]-pyridin-3-yl] acetamide | 21 | 63 | 439.1 |
| 23 | 2-Thiophen-2-yl-N-[2-[3-[3-(trifluoromethyl)phenyl-propylsulfanyl]-pyridin-3-yl] acetamide | 21 | 72 | 437.1 |
| 24 | 2-Naphthalen-2-yl-N-[2-[2-[[3-(trifluoromethyl)phenyl]sulfonyl]-ethylsulfanyl]-pyridin-3-yl] acetamide | 14 | 73 | 531.1 |
| 25 | 4-Phenyl-N-[2-[2-[[3-(trifluoromethyl)phenyl]sulfonyl]-ethylsulfanyl]-pyridin-3-yl]-butyramide | 14 | 72 | 509.1 |
| 26 | 3-Thiophen-2-yl-N-[2-[2-[[3-(trifluoromethyl)phenyl]sulfonyl]-ethylsulfanyl]-pyridin-3-yl] propionamide | 14 | 57 | 501.1 |
| 27 | 3-Phenyl-N-[2-[2-[[3-(trifluoromethyl)phenyl]sulfonyl]-ethylsulfanyl]-pyridin-3-yl] propionamide | 14 | 53 | 495.1 |
| 28 | 3-Cyclopentyl-N-[2-[2-[[3-(trifluoromethyl)phenyl]sulfonyl]-ethylsulfanyl]-pyridin-3-yl] propionamide | 14 | 75 | 487.1 |
| 29 | 2-Cyclohexyl-N-[2-[2-[[3-(trifluoromethyl)phenyl]sulfanyl]-ethylsulfanyl]-pyridin-3-yl] acetamide | 21 | 44 | 455.1 |
| 31 | (E)-3-(4-Fluorophenyl)-N-[2-[2-[[3-(trifluoromethyl)phenyl]sulfonyl]-ethylsulfanyl]-pyridin-3-yl] acrylamide | 14 | 63 | 511.1 |
| 33 | N-[2-(3-Phenyl-propylsulfanyl)-pyridin-3-yl]-2-thiophen-2-yl acetamide | 21 | 62 | 369.1 |
| 35 | 6-Chloro-N-[2-[2-[[3-(trifluoromethyl)phenyl]sulfonyl]-ethylsulfanyl]-pyridin-3-yl]-pyridine-3-carboxylic acid amide | 14 | 77 | 502 |
| 36 | 2-Pyridin-4-yl-N-[2-[2-[[3-(trifluoromethyl)phenyl]sulfonyl]-ethylsulfanyl]-pyridin-3-yl] acetamide | 14 | 44 | 482.1 |
| 37 | 2-(3-Hydroxyphenyl)-N-[2-[2-[[3-(trifluoromethyl)phenyl]sulfonyl]-ethylsulfanyl]-pyridin-3-yl] acetamide | 12 | 58 | 497.1 |
| 38 | N-[2-[2-[[3-(Trifluoromethyl)phenyl]sulfonyl]-ethylsulfanyl]-pyridin-3-yl]-tetrahydropyrane-3-carboxylic acid amide | 14 | 65 | 475.1 |
| 39 | 2-Tetrahydropyran-2-yl-N-[2-[2-[[3-(trifluoromethyl)phenyl]sulfonyl]-ethylsulfanyl]-pyridin-3-yl] acetamide | 14 | 58 | 489.1 |
| 40 | 2-Tetrahydropyran-4-yl-N-[2-[2-[[3-(trifluoromethyl)phenyl]sulfonyl]-ethylsulfanyl]-pyridin-3-yl] acetamide | 14 | 61 | 489.1 |
| 41 | 3-Cyclohexyl-N-[2-[2-[[3-(trifluoromethyl)phenyl]sulfonyl]-ethylsulfanyl]-pyridin-3-yl] propionamide | 14 | 77 | 501.1 |
| 44 | 2-Cyclohexyl-N-[2-(2-phenylsulfanyl-ethylsulfanyl)-pyridin-3-yl] acetamide | 21 | 27 | 387.1 |
| 45 | N-[2-(2-Phenoxy-ethylsulfanyl)-pyridin-3-yl]-2-thiophen-2-yl acetamide | 21 | 66 | 371.1 |
| 46 | 2-Pyridin-3-yl-N-[2-[2-[[3-(trifluoromethyl)phenyl]sulfonyl]-ethylsulfanyl]-pyridin-3-yl] acetamide | 14 | 55 | 482.1 |
| 47 | 3-Hydroxy-N-[2-[2-[[3-(trifluoromethyl)phenyl]sulfonyl]-ethylsulfanyl]-pyridin-3-yl] benzamide | 14 | 52 | 483.1 |

TABLE 2-continued

| Example | Chemical name | Preparation analogous to example | Yield [%] | MS m/z [M+H]+ |
|---|---|---|---|---|
| 48 | N-[2-[2-[[3-(Trifluoromethyl)phenyl]sulfonyl]-ethylsulfanyl]-pyridin-3-yl]-tetrahydropyrane-2-carboxylic acid amide | 14 | 45 | 475.1 |
| 49 | 2-Cycloheptyl-N-[2-[2-[[3-(trifluoromethyl)phenyl]sulfonyl]-ethylsulfanyl]-pyridin-3-yl] acetamide | 14 | 64 | 501.1 |
| 52 | 2-(1,2,3,4-Tetrahydronaphthalen-2-yl)-N-[2-[2-[[3-(trifluoromethyl)phenyl]sulfonyl]-ethylsulfanyl]-pyridin-3-yl] acetamide | 14 | 58 | 535.1 |
| 53 | 2-Hydroxy-N-[2-[2-[[3-(trifluoromethyl)phenyl]sulfonyl]-ethylsulfanyl]-pyridin-3-yl] benzamide | 14 | 31 | 483.1 |
| 56 | N-[4-Methyl-2-[2-[[3-(trifluoromethyl)phenyl]sulfonyl]-ethylsulfanyl]-pyridin-3-yl]-2-thiophen-2-yl acetamide | 1 | 49 | 501.1 |
| 57 | 3-(1,2,3,4-Tetrahydronaphthalen-2-yl)-N-[2-[2-[[3-(trifluoromethyl)phenyl]sulfonyl]-ethylsulfanyl]-pyridin-3-yl propionamide | 14 | 52 | 549.1 |
| 58 | 3-Cycloheptyl-N-[2-[2-[[3-(trifluoromethyl)phenyl]sulfonyl]-ethylsulfanyl]-pyridin-3-yl] propionamide | 14 | 47 | 515.2 |
| 59 | 2-(Benzo[b]thiophen-2-yl)-N-[2-[2-[[3-(trifluoromethyl)phenyl]sulfonyl]-ethylsulfanyl]-pyridin-3-yl] acetamide | 14 | 54 | 537.1 |
| 61 | N-[2-[2-[(4-Fluorophenyl)sulfanyl]-ethylsulfanyl]-pyridin-3-yl]-3,3-dimethyl butyramide | 1 | 74 | 379.1 |
| 62 | 2-(5-Bicyclo[2.2.1]heptanyl)-N-[2-[2-[[3-(trifluoromethyl)phenyl]sulfonyl]-ethylsulfanyl]-pyridin-3-yl] acetamide | 14 | 55 | 499.1 |
| 63 | N-[2-[2-(4-Fluorophenoxy)-ethylsulfanyl]-pyridin-3-yl]-3,3-dimethyl butyramide | 1 | 35 | 363.1 |
| 64 | 3,4-Difluoro-N-[2-[2-(4-fluorophenoxy)-ethylsulfanyl]-pyridin-3-yl] benzamide | 1 | 55 | 405.1 |
| 65 | 3,4-Difluoro-N-[2-[3-(4-fluorophenyl)-propylsulfanyl]-pyridin-3-yl] benzamide | 1 | 60 | 403.1 |
| 66 | N-[2-[3-(4-Fluorophenyl)-propylsulfanyl]-pyridin-3-yl]-3,3-dimethyl butyramide | 1 | 48 | 361.2 |
| 67 | 2-Cycloheptyl-N-[2-[2-[(4-fluorophenyl)sulfonyl]-ethylsulfanyl]-pyridin-3-yl] acetamide | 14 | 18 | 451.1 |
| 68 | 2-Cyclohexyl-2,2-difluoro-N-[2-[2-[[3-(trifluoromethyl)phenyl]sulfonyl]-ethylsulfanyl]-pyridin-3-yl] acetamide | 55 | 11 | 523.1 |

Pharmacological Experiments

Fluorescence Assay Using a Voltage-Sensitive Dye

Human CHO-K1 cells expressing KCNQ2/3 channels are cultivated adherently at 37° C., 5% $CO_2$ and 95% humidity in cell culture bottles (e.g. 80 $cm^2$ TC flasks, Nunc) with DMEM-high glucose (Sigma Aldrich, D7777) including 10% FCS (PAN Biotech, e.g. 3302-P270521) or alternatively MEM Alpha Medium (1×, liquid, Invitrogen, #22571), 10% foetal calf serum (FCS) (Invitrogen, #10270-106, heat-inactivated) and the necessary selection antibiotics.

Before being seeded out for the measurements, the cells are washed with a 1×DPBS buffer without $Ca^{2+}/Mg^{2+}$ (e.g. Invitrogen, #14190-094) and detached from the bottom of the culture vessel by means of Accutase (PAA Laboratories, #L11-007) (incubation with Accutase for 15 min at 37° C.). The cell count then present is determined using a CASY™ cell counter (TCC model, Schärfe System) in order subsequently to apply 20,000 to 30,000 cells/well/100 µl of the described nutrient medium, depending on density optimisation for the individual cell line, to 96-well measuring plates of the Corning™ CellBIND™ type (flat clear-bottom black polystyrene microplates, #3340). Incubation is then carried out for one hour at room temperature, without gassing or adjusting the humidity, followed by incubation for 24 hours at 37° C., 5% $CO_2$ and 95% humidity.

The voltage-sensitive fluorescent dye from the Membrane Potential Assay Kit (Red™ bulk format part R8123 for FLIPR, MDS Analytical Technologies™) is prepared by dissolving the contents of a vessel of Membrane Potential Assay Kit Red Component A in 200 ml of extracellular buffer (ES buffer, 120 mM NaCl, 1 mM KCl, 10 mM HEPES, 2 mM $CaCl_2$, 2 mM $MgCl_2$, 10 mM glucose; pH 7.4). After removal of the nutrient medium, the cells are washed with 200 µl of ES buffer, then covered with a layer of 100 µl of the dye solution prepared above and incubated for 45 min at room temperature with exclusion of light.

The fluorescence measurements are carried out with a BMG Labtech FLUOstar™, BMG Labtech NOVOstar™ or BMG Labtech POLARstar™ instrument (525 nm excitation, 560 nm emission, bottom-read mode). After incubation of the dye, 50 µl of the substances to be tested in the desired concentrations, or 50 µl of ES buffer for control purposes, are introduced into separate cavities of the measuring plate and incubated for 30 min at room temperature whilst being shielded from light. The fluorescence intensity of the dye is then measured for 5 min and the fluorescence value $F_1$ of each well is thus determined at a given, constant time. 15 µl of a 100 mM KCl solution (final concentration 92 mM) are then added to each well. The change in fluorescence is subsequently measured until all relevant measured values have been obtained (mainly S-30 min). At a given time after KCl application, a fluorescence value $F_2$ is determined, in this case at the time of the fluorescence peak.

For calculation, the fluorescence intensity $F_2$ is compared with the fluorescence intensity $F_1$, and the agonistic activity of the target compound on the potassium channel is determined therefrom. $F_2$ and $F_1$ are calculated as follows:

$$\left(\frac{F_2 - F_1}{F_1}\right) \times 100 = \frac{\Delta F}{F}(\%)$$

In order to determine whether a substance has an agonistic activity, $$\frac{\Delta F}{F},$$

for example, can be compared with $$\left(\frac{\Delta F}{F}\right)_K$$

of control cells.

$$\left(\frac{\Delta F}{F}\right)_K$$

is determined by adding to the reaction batch only the buffer solution instead of the substance to be tested, determining the value $F_{1K}$ of the fluorescence intensity, adding the potassium ions as described above and measuring a value $F_{2K}$ of the fluorescence intensity. Then $F_{2K}$ and $F_{1K}$ are calculated as follows:

$$\left(\frac{F_{2K} - F_{1K}}{F_{1K}}\right) \times 100 = \left(\frac{\Delta F}{F}\right)_K(\%)$$

A substance has an agonistic activity on the potassium channel if $$\frac{\Delta F}{F}$$

is greater than $$\left(\frac{\Delta F}{F}\right)_K:$$

$$\frac{\Delta F}{F} \rangle \left(\frac{\Delta F}{F}\right)_K$$

Independently of the comparison of $$\frac{\Delta F}{F}$$

with $$\left(\frac{\Delta F}{F}\right)_K,$$

it is also possible to conclude that a target compound has an agonistic activity if an increase in $$\frac{\Delta F}{F}$$

is to be observed as the dosage of the target compound increases.

Calculations of $EC_{50}$ values are carried out with the aid of Prism v4.0 software (GraphPad Softwares™).

Formalin Test in Mice

The formalin test (Dubuisson, D. and Dennis, S. G., 1977, Pain, 4, 161-174) is a model for acute and chronic pain. A single formalin injection into the dorsal side of one rear paw is used to induce a biphase nociceptive response in experimental animals allowed to move freely, and the response is recorded by observation of three clearly distinguishable behaviour patterns. The response comprises two phases: phase 1=immediate response (duration up to 10 min; shaking of paw, licking), phase 2=delayed response (after a rest phase; likewise shaking of paw, licking; duration up to 60 min). Phase 1 reflects a direct stimulation of the peripheral nocisensors with a high spinal nociceptive input (acute pain phase); phase 2 reflects a spinal and peripheral hypersensitisation (chronic pain phase). In the experiments presented here the chronic pain component (phase 2) was evaluated.

Formalin is administered subcutaneously in a volume of 20 µl and a concentration of 1% into the dorsal side of the right rear paw of each animal. The specific behavioural changes, such as lifting, shaking or licking the paw (score 3, Dubuisson & Dennis, 1977), were observed and recorded during the observation period of 21 to 24 min after formalin injection. The behaviour of the animals after administration of the substance (n=10 per substance dose) was compared with that of a control group to which a vehicle was administered (n=10).

Based on the quantification of the pain behaviour, the effect of the substance in the formalin test was determined as the change in comparison to the control as a percentage. The $ED_{50}$ ($ED_{50}$=average effective dose) was calculated by means of regression analysis using the method defined by Litchfield and Wilcoxon (Litchfield, J. T., Wilcoxon, J. J., 1949, J. Pharmacol. Exp. Ther. 96, 99-113). The time at which the compound was administered ahead of the formalin injection was 5 min in the case of intravenous administration and 30 min in the case of oral administration.

Pharmacological Data

The results of the pharmacological models described above are summarised in Table 3.

TABLE 3

| Ex. no. | Fluorimetry % efficacy (I/EC50, retigabine = 100%) | Fluorimetry EC50 [nM] | Fluorimetry IC50 [nM] | Formalin test in mice IV Effect @ dose [mg/kg] |
|---|---|---|---|---|
| 1 | 172 | 95 | | |
| 2 | 142 | 27 | | |
| 3 | 164 | 31 | | 87% @ 4.64 |
| 4 | 55 | | | |
| 5 | 129 | 469 | | |
| 6 | 225 | 76 | | |
| 7 | 125 | 424 | | |
| 8 | −68 | | 322 | |
| 9 | −45 | | 192 | |
| 10 | 74 | 55 | | |
| 11 | 109 | 588 | | |
| 12 | 141 | 168 | | |
| 13 | 46 | | | |
| 14 | 167 | 45 | | |
| 18 | 43 | 457 | | |
| 19 | −43 | | | |
| 20 | 97 | 180 | | |
| 21 | 152 | 83 | | |
| 22 | 155 | 732 | | |
| 23 | 165 | 157 | | |
| 24 | 84 | 153 | | |
| 25 | 170 | 71 | | |
| 26 | 82 | 123 | | |
| 27 | 112 | 208 | | |
| 28 | 152 | 277 | | |
| 29 | 108 | 312 | | |
| 31 | 109 | 841 | | |
| 33 | 106 | 141 | | |
| 35 | 43 | | | |
| 36 | 38 | | | |
| 37 | 31 | | | |
| 38 | 35 | | | |
| 39 | 139 | 363 | | |
| 40 | 52 | | | |
| 41 | 127 | 99 | | |
| 44 | 80 | 153 | | |
| 45 | 58 | | | |
| 46 | 50 | | | |
| 47 | 95 | 265 | | |
| 48 | 93 | 174 | | |
| 49 | 108 | 19 | | |
| 50 | | | | |
| 51 | 32 | 106 | | |
| 52 | 59 | 208 | | |
| 53 | 27.45 | | | |
| 55 | 84.85 | 3600 | | |
| 56 | 98.1 | 348.5 | | |
| 57 | 134 | 56.5 | | |
| 58 | 167.4 | 47.5 | | |
| 59 | 138.55 | 925 | | |
| 60 | 101 | 1025 | | |
| 61 | 128.55 | 27.5 | | |
| 62 | 168.4 | 23.5 | | |
| 63 | 119 | 546 | | |
| 64 | 49 | 200 | | |
| 65 | 148 | 480 | | |
| 66 | 176 | 184 | | |
| 67 | 114 | 18 | | |
| 68 | 79 | 22 | | |

The invention claimed is:

1. A substituted N-(2-mercaptopyridin-3-yl)amide having the formula (1):

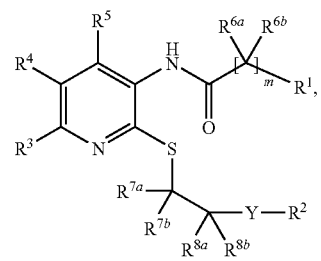

wherein m stands for 0, 1, 2 or 3;

$R^1$ stands for $C_{1-6}$ alkyl, saturated or unsaturated, branched or unbranched, unsubstituted or mono- or polysubstituted; $C_{3-10}$ cycloalkyl or heterocyclyl, each saturated or unsaturated, unsubstituted or mono- or polysubstituted; aryl or heteroaryl, each unsubstituted or mono- or polysubstituted;

with the proviso that if $R^1$ denotes heterocyclyl, the heterocyclyl is bound via a carbon atom in the heterocyclyl;

$R^2$ stands for aryl or heteroaryl, each unsubstituted or mono- or polysubstituted;

Y is selected from the group consisting of —$(CR^{9a}R^{9b})$—, $SO_2$, $S(=O)$, —S—, —O—, $C(=O)$;

$R^3$, $R^4$, $R^5$, $R^{6a}$, $R^{6b}$, $R^{7a}$, $R^{7b}$, $R^{8a}$, $R^{8b}$, $R^{9a}$ and $R^{9b}$ each stand independently of one another for H; F; Cl; Br; I; $NO_2$; $CF_3$; CN; OH; $OCF_3$; SH; $SCF_3$; $NH_2$; $C_{1-6}$ alkyl, O—$C_{1-6}$ alkyl, O—C(=O)—$C_{1-6}$ alkyl, S—$C_{1-6}$ alkyl, NH($C_{1-6}$ alkyl), N($C_{1-6}$ alkyl)$_2$, NH—C(=O)—$C_{1-6}$ alkyl, N(C(=O)—$C_{1-6}$ alkyl)$_2$ or C(=O)—$C_{1-6}$ alkyl, each saturated or unsaturated, branched or unbranched, unsubstituted or mono- or polysubstituted; $C_{3-7}$ cycloalkyl or heterocyclyl, each saturated or unsaturated, branched or unbranched, unsubstituted or mono- or polysubstituted;

wherein $R^{7a}$ can form with $R^{8a}$ a $C_{3-7}$ cycloalkyl radical, which can be saturated or unsaturated, unsubstituted or mono- or polysubstituted;

wherein "substituted" in the case of substitution on alkyl stands for the substitution of one or more hydrogen atoms each independently of one another by F; Cl; Br; I; $NO_2$; $CF_3$; CN; $C_{1-8}$ alkyl; $C_{2-8}$ heteroalkyl; aryl; heteroaryl; $C_{3-10}$ cycloalkyl; heterocyclyl; $C_{1-8}$ alkyl- or $C_{2-8}$ heteroalkyl-bridged aryl, heteroaryl, $C_{3-10}$ cycloalkyl or heterocyclyl; CHO; C(=O)$C_{1-8}$ alkyl; C(=O)aryl; C(=O)heteroaryl; $CO_2H$; C(=O)O—$C_{1-8}$ alkyl; C(=O)O-aryl; C(=O)O-heteroaryl; $CONH_2$; C(=O)NH—$C_{1-8}$ alkyl; C(=O)N($C_{1-8}$ alkyl)$_2$; C(=O)NH-aryl; C(=O)N(aryl)$_2$; C(=O)NH-heteroaryl; C(=O)N(heteroaryl)$_2$; C(=O)N($C_{1-8}$ alkyl)(aryl); C(=O)N($C_{1-8}$ alkyl)(heteroaryl); C(=O)N(heteroaryl)(aryl); OH; O—$C_{1-8}$ alkyl; $OCF_3$; O—($C_{1-8}$ alkyl)-OH; O—($C_{1-8}$ alkyl)-O—$C_{1-8}$ alkyl; O-benzyl; O-aryl; O-heteroaryl; O—C(=O)$C_{1-8}$ alkyl; O—C(=O)aryl; O—C(=O)heteroaryl; $NH_2$; NH—$C_{1-8}$ alkyl; N($C_{1-8}$ alkyl)$_2$; NH—C(=O)$C_{1-8}$ alkyl; N($C_{1-8}$ alkyl)-C(=O) $C_{1-8}$ alkyl; N(C(=O)$C_{1-8}$ alkyl)$_2$; NH—C(=O)-aryl; NH—C(=O)-heteroaryl; SH; S—$C_{1-8}$ alkyl; $SCF_3$; S-benzyl; S-aryl; S-heteroaryl; $S(=O)_2C_{1-8}$ alkyl; $S(=O)_2$aryl; $S(=O)_2$heteroaryl; $S(=O)_2OH$;

S(=O)₂O—C₁₋₈ alkyl; S(=O)₂O-aryl; S(=O)₂O-heteroaryl; S(=O)₂—NH—C₁₋₈ alkyl; S(=O)₂—NH-aryl; and S(=O)₂—NH—C₁₋₈-heteroaryl;

wherein "substituted" in the case of substitution on heterocyclyl and cycloalkyl stands for the substitution of one or more hydrogen atoms each independently of one another by F; Cl; Br; I; NO₂; CF₃; =O; CN; C₁₋₈ alkyl; C₂₋₈ heteroalkyl; aryl; heteroaryl; C₃₋₁₀ cycloalkyl; heterocyclyl; C₁₋₈ alkyl- or C₂₋₈ heteroalkyl-bridged aryl, heteroaryl, C₃₋₁₀ cycloalkyl or heterocyclyl; CHO; C(=O)C₁₋₈ alkyl; C(=O)aryl; C(=O)heteroaryl; CO₂H; C(=O)O—C₁₋₈ alkyl; C(=O)O-aryl; C(=O)O-heteroaryl; CONH₂; C(=O)NH—C₁₋₈ alkyl; C(=O)N(C₁₋₈ alkyl)₂; C(=O)NH-aryl; C(=O)N(aryl)₂; C(=O)NH-heteroaryl; C(=O)N(heteroaryl)₂; C(=O)N(C₁₋₈ alkyl)(aryl); C(=O)N(C₁₋₈ alkyl)(heteroaryl); C(=O)N(heteroaryl)(aryl); OH; O—C₁₋₈ alkyl; OCF₃; O—(C₁₋₈ alkyl)-OH; O—(C₁₋₈ alkyl)-O—C₁₋₈ alkyl; O-benzyl; O-aryl; O-heteroaryl; O—C(=O)C₁₋₈ alkyl; O—C(=O)aryl; O—C(=O)heteroaryl; NH₂; NH—C₁₋₈ alkyl; N(C₁₋₈ alkyl)₂; NH—C(=O)C₁₋₈ alkyl; N(C₁₋₈ alkyl)-C(=O)C₁₋₈ alkyl; N(C(=O)C₁₋₈ alkyl)₂; NH—C(=O)-aryl; NH—C(=O)-heteroaryl; SH; S—C₁₋₈ alkyl; SCF₃; S-benzyl; S-aryl; S-heteroaryl; S(=O)₂C₁₋₈ alkyl; S(=O)₂ aryl; S(=O)₂ heteroaryl; S(=O)₂OH; S(=O)₂O—C₁₋₈ alkyl; S(=O)₂O-aryl; S(=O)₂O-heteroaryl; S(=O)₂—NH—C₁₋₈ alkyl; S(=O)₂—NH-aryl; and S(=O)₂—NH—C₁₋₈ heteroaryl;

wherein "substituted" in the case of substitution on aryl or heteroaryl stands for the substitution of one or more hydrogen atoms each independently of one another by F; Cl; Br; I; NO₂; CF₃; CN; C₁₋₈ alkyl; or C₂₋₈ heteroalkyl; aryl; heteroaryl; C₃₋₁₀ cycloalkyl; heterocyclyl; C₁₋₈ alkyl- or C₂₋₈ heteroalkyl-bridged aryl, heteroaryl, C₃₋₁₀ cycloalkyl or heterocyclyl; CHO; C(=O)C₁₋₈ alkyl; C(=O)aryl; C(=O)heteroaryl; CO₂H; C(=O)O—C₁₋₈ alkyl; C(=O)O-aryl; C(=O)O-heteroaryl; CONH₂; C(=O)NH—CH₃; C(=O)NH—C₂H₅; C(=O)N(C₁₋₈ alkyl)₂; C(=O)NH-aryl; C(=O)N(aryl)₂; C(=O)NH-heteroaryl; C(=O)N(heteroaryl)₂; C(=O)N(C₁₋₈ alkyl)(aryl); C(=O)N(C₁₋₈ alkyl)(heteroaryl); C(=O)N(heteroaryl)(aryl); OH; O—C₁₋₈ alkyl; OCF₃; O—(C₁₋₈ alkyl)-OH; O—(C₁₋₈ alkyl)-O—C₁₋₈ alkyl; O-benzyl; O-aryl; O-heteroaryl; O—C(=O)C₁₋₈ alkyl; O—C(=O)aryl; O—C(=O)heteroaryl; NH₂; NH—C₁₋₈ alkyl; N(C₁₋₈ alkyl)₂; NH—C(=O)C₁₋₈ alkyl; N(C₁₋₈ alkyl)-C(=O)C₁₋₈ alkyl; N(C(=O)C₁₋₈ alkyl)₂; NH—C(=O)-aryl; NH—C(=O)-heteroaryl; SH; S—C₁₋₈ alkyl; SCF₃; S-benzyl; S-aryl; S-heteroaryl; S(=O)₂C₁₋₈ alkyl; S(=O)₂aryl; S(=O)₂heteroaryl; S(=O)₂OH; S(=O)₂O—C₁₋₈ alkyl; S(=O)₂O-aryl; S(=O)₂O-heteroaryl; S(=O)₂—NH—C₁₋₈ alkyl; S(=O)₂—NH-aryl; S(=O)₂—NH—C₁₋₈ heteroaryl;

said substituted N-(2-mercaptopyridin-3-yl)amide being in the form of a free compound or a salt thereof with a physiologically compatible acid or base.

2. Substituted pyridinylamide according to claim 1, or salt thereof, wherein $R^1$ stands for phenyl, pyridyl or thienyl, each unsubstituted or mono- or polysubstituted with one or more substituents each selected independently of one another from the group consisting of F, Cl, Br, I, NO₂, CF₃, CN, methyl, ethyl, n-propyl, isopropyl, cyclopropyl, n-butyl, sec-butyl, tert-butyl, CH₂CF₃, C(=O)-methyl, C(=O)-ethyl, C(=O)—OH, C(=O)—O-methyl, C(=O)—O-ethyl, C(=O)—NH₂, C(=O)—N(methyl)₂, C(=O)—N(ethyl)₂, C(=O)—NH-methyl, C(=O)—NH-ethyl, C(=O)—N(methyl)(ethyl), OH, O-methyl, O-ethyl, O—(CH₂)₂—O—CH₃, O—(CH₂)₂—OH, OCF₃, O—C(=O)-methyl, O—C(=O)-ethyl, NR$^a$R$^b$, wherein R$^a$ and R$^b$ are each selected independently of one another from the group consisting of H, methyl, ethyl, (CH₂)₂—O—CH₃ and (CH₂)₂—OH or R$^a$ and R$^b$ together with the nitrogen atom linking them form a pyrrolidinyl, piperidinyl, 4-methylpiperazinyl or morpholinyl, NHC(=O)-methyl, NHC(=O)-ethyl, SH, SCF₃, S-methyl, S-ethyl, S(=O)₂OH, S(=O)₂O-methyl, benzyl, phenyl, pyridyl, wherein benzyl, phenyl, pyridyl are each unsubstituted or mono-, di- or trisubstituted with one, two or three substituents each selected independently of one another from the group consisting of F, Cl, Br, I, CN, methyl, ethyl, CF₃, OH, O-methyl and OCF₃.

3. Substituted pyridinylamide according to claim 1, or salt thereof, wherein $R^1$ stands for phenyl, pyridyl or thienyl, each unsubstituted or mono- or di- or trisubstituted with one, two or three substituents each selected independently of one another from the group consisting of F, Cl, Br, I, NO₂, CF₃, CN, methyl, ethyl, C(=O)-methyl, OH, O-methyl, O—(CH₂)₂—O—CH₃, OCF₃, O—C(=O)-methyl, NH₂, NH—C(=O)-methyl, N(methyl)₂, morpholinyl, S-methyl, SCF₃, benzyl and phenyl.

4. Substituted pyridinylamide according to claim 1, or salt thereof, wherein $R^2$ stands for aryl or heteroaryl, each unsubstituted or mono- or polysubstituted with one or more substituents, each selected independently of one another from the group consisting of F, Cl, Br, I, NO₂, CN, OH, O—C₁₋₈ alkyl, OCF₃, C₁₋₈ alkyl, C(=O)—OH, CF₃, NH₂, NH(C₁₋₈ alkyl), N(C₁₋₈ alkyl)₂, SH, S—C₁₋₈ alkyl, SCF₃, S(=O)₂OH, benzyl, phenyl, pyridyl and thienyl, wherein benzyl, phenyl, pyridyl, thienyl can each be unsubstituted or mono- or polysubstituted with one or more substituents selected independently of one another from the group consisting of F, Cl, Br, I, NO₂, CN, OH, O—C₁₋₈ alkyl, OCF₃, C₁₋₈ alkyl, C(=O)—OH, CF₃, NH₂, NH(C₁₋₈ alkyl), N(C₁₋₈ alkyl)₂, SH, S—C₁₋₈ alkyl, SCF₃, and S(=O)₂OH.

5. Substituted pyridinylamide according to claim 1, or salt thereof, wherein the radical $R^2$ stands for aryl or heteroaryl, each unsubstituted or mono- or polysubstituted with one or more substituents, each selected independently of one another from the group consisting of F, Cl, Br, I, NO₂, CN, OH, O—C₁₋₈ alkyl, OCF₃, C₁₋₈ alkyl, C(=O)—OH, CF₃, NH₂, NH(C₁₋₈ alkyl), N(C₁₋₈ alkyl)₂, SH, S—C₁₋₈ alkyl, SCF₃, S(=O)₂OH, benzyl, phenyl, pyridyl and thienyl, wherein benzyl, phenyl, pyridyl, thienyl can each be unsubstituted or mono- or polysubstituted with one or more substituents selected independently of one another from the group consisting of F, Cl, Br, I, NO₂, CN, OH, O—C₁₋₈ alkyl, OCF₃, C₁₋₈ alkyl, C(=O)—OH, CF₃, NH₂, NH(C₁₋₈ alkyl), N(C₁₋₈ alkyl)₂, SH, S—C₁₋₈ alkyl, SCF₃, and S(=O)₂OH.

6. Substituted pyridinylamide according to claim 1, or salt thereof, wherein $R^{7a}$, $R^{7b}$, $R^{8a}$, $R^{8b}$, $R^{9a}$ and $R^{9b}$ each stand independently of one another for H; F; Cl; Br; I; NO₂; CF₃; CH₂CF₃; CN; OH; OCF₃, NH₂; C₁₋₄ alkyl, O—C₁₋₄ alkyl, O—C₁₋₄ alkyl-OH, O—C₁₋₄ alkyl-O—CH₃, NH—C₁₋₄ alkyl, N(C₁₋₄ alkyl)₂, each saturated or unsaturated, branched or unbranched, unsubstituted; C₃₋₁₀ cycloalkyl, saturated or unsaturated, unsubstituted or mono- or polysubstituted with one or more substituents each selected independently of one another from the group consisting of F, Cl, Br, I, C₁₋₄ alkyl, OH, and O—C₁₋₄ alkyl.

7. Substituted pyridinylamide according to claim 1, or salt thereof, wherein $R^{7a}$ forms with $R^{8a}$ a 6-membered cycloalkyl radical, which can be saturated or unsaturated, unsubstituted or mono- or polysubstituted.

8. Substituted pyridinylamide according to claim 1, or salt thereof, wherein m=0 or 1.

9. Substituted pyridinylamide according to claim 1, or salt thereof, wherein Y stands for —(CR$^{9a}$R$^{9b}$)—.

10. Substituted pyridinylamide according to claim 1, or salt thereof, wherein R$^3$, R$^4$ and R$^5$ each stand independently of one another for H; F; Cl; Br; I; NO$_2$; CF$_3$; CN; OH; OCF$_3$; SH; SCF$_3$; methyl; ethyl; n-propyl; isopropyl; butyl; sec-butyl; tert-butyl; CH$_2$CF$_3$; O-methyl; O-ethyl; O-n-propyl; O-isopropyl; O-butyl; O-sec-butyl; O-tert-butyl; O—(CH$_2$)$_2$—O-methyl; O—(CH$_2$)$_2$—OH; O—(C═O)-methyl; O—(C═O)-ethyl; S-methyl; S-ethyl; cyclopropyl; cyclobutyl; or NR$^a$R$^b$, wherein R$^a$ and R$^b$ are each selected independently of one another from the group consisting of H, methyl, ethyl, (CH$_2$)$_2$—O-methyl, (CH$_2$)$_2$—OH, (C═O)-methyl, and (C═O)-ethyl or R$^a$ and R$^b$ together with the nitrogen atom linking them form a pyrrolidinyl, piperidinyl, 4-methylpiperazinyl or morpholinyl.

11. Substituted pyridinylamide according to claim 1, or salt thereof, wherein m stands for the number 0 and R$^1$ stands for aryl or heteroaryl;

m stands for the number 1 and R$^1$ stands for thienyl, phenyl, a C$_{3-8}$ alkyl radical, which can be saturated or unsaturated, unsubstituted or mono- or polysubstituted, or a monocyclic or bicyclic C$_{3-8}$ cycloalkyl radical, which can be saturated or unsaturated (but not aromatic), unsubstituted or mono- or polysubstituted; or m stands for the number 2 and R$^1$ stands for phenyl, cycloalkyl or alkyl.

12. Substituted pyridinylamide according to claim 1, selected from the group consisting of:

N-[2-[2-(Benzenesulfonyl)-ethylsulfanyl]-pyridin-3-yl]-2-cyclohexyl acetamide;

2-Cyclohexyl-N-[2-[2-[[3-(trifluoromethyl)phenyl]sulfonyl]-ethylsulfanyl]-pyridin-3-yl]acetamide;

2-Thiophen-2-yl-N-[2-[2-[[3-(trifluoromethyl)phenyl]sulfonyl]-ethylsulfanyl]-pyridin-3-yl]acetamide;

N-[2-[2-(Benzenesulfonyl)-ethylsulfanyl]-pyridin-3-yl] benzamide;

N-[2-[2-(Benzenesulfonyl)-ethylsulfanyl]-pyridin-3-yl]-3,4-difluorobenzamide;

N-[2-[2-(Benzenesulfonyl)-ethylsulfanyl]-pyridin-3-yl]-3-cyclohexyl propionamide;

N-[2-[2-(Benzenesulfonyl)-ethylsulfanyl]-pyridin-3-yl]-2-thiophen-2-yl acetamide;

N-[2-[2-(Benzenesulfonyl)-ethylsulfanyl]-pyridin-3-yl]-2-(3,5-dimethylphenyl) propionamide;

2-(2-Methoxyphenyl)-N-[2-[2-[[3-(trifluoromethyl)phenyl]sulfonyl]-ethylsulfanyl]-pyridin-3-yl]acetamide;

2-(4-Methoxyphenyl)-N-[2-[2-[[3-(trifluoromethyl)phenyl]sulfonyl]-ethylsulfanyl]-pyridin-3-yl]acetamide;

2-(3-Methoxyphenyl)-N-[2-[2-[[3-(trifluoromethyl)phenyl]sulfonyl]-ethylsulfanyl]-pyridin-3-yl]acetamide 2-(2-Hydroxyphenyl)-N-[2-[2-[[3-(trifluoromethyl)phenyl]sulfonyl]-ethylsulfanyl]-pyridin-3-yl]acetamide;

2-(4-Hydroxyphenyl)-N-[2-[2-[[3-(trifluoromethyl)phenyl]sulfonyl]-ethylsulfanyl]-pyridin-3-yl]acetamide;

2-Cyclopentyl-N-[2-[2-[[3-(trifluoromethyl)phenyl]sulfonyl]-ethylsulfanyl]-pyridin-3-yl]acetamide;

N-[2-[2-[[3-(Trifluoromethyl)phenyl]sulfonyl]-ethylsulfanyl]-pyridin-3-yl]-thiophene-2-carboxylic acid amide;

4-9 N-[2-[2-[[3-(Trifluoromethyl)phenyl]sulfonyl]-ethylsulfanyl]-pyridin-3-yl]-cyclohexane carboxylic acid amide;

2-Thiophen-2-yl-N-[2-[2-[[3-(trifluoromethyl)phenyl]sulfanyl]-ethylsulfanyl]-pyridin-3-yl]acetamide;

N-[2-(2-Phenylsulfanyl-ethylsulfanyl)-pyridin-3-yl]-2-thiophen-2-yl acetamide;

2-Thiophen-2-yl-N-[2-[2-[3-(trifluoromethyl)-phenoxy]-ethylsulfanyl]-pyridin-3-yl]acetamide;

2-Thiophen-2-yl-N-[2-[2-[3-[3-(trifluoromethyl)phenyl]-propylsulfanyl]-pyridin-3-yl]acetamide;

2-Naphthalen-2-yl-N-[2-[2-[[3-(trifluoromethyl)phenyl]sulfonyl]-ethylsulfanyl]-pyridin-3-yl]acetamide;

4-Phenyl-N-[2-[2-[[3-(trifluoromethyl)phenyl]sulfonyl]-ethylsulfanyl]-pyridin-3-yl]-butyramide;

3-Thiophen-2-yl-N-[2-[2-[[3-(trifluoromethyl)phenyl]sulfonyl]-ethylsulfanyl]-pyridin-3-yl]propionamide;

3-Phenyl-N-[2-[2-[[3-(trifluoromethyl)phenyl]sulfonyl]-ethylsulfanyl]-pyridin-3-yl]propionamide;

3-Cyclopentyl-N-[2-[2-[[3-(trifluoromethyl)phenyl]sulfonyl]-ethylsulfanyl]-pyridin-3-yl]propionamide;

2-Cyclohexyl-N-[2-[2-[[3-(trifluoromethyl)phenyl]sulfanyl]-ethylsulfanyl]-pyridin-3-yl]acetamide;

(E)-3-(4-Fluorophenyl)-N-[2-[2-[[3-(trifluoromethyl)phenyl]sulfonyl]-ethylsulfanyl]-pyridin-3-yl]acrylamide;

N-[2-(3-Phenyl-propylsulfanyl)-pyridin-3-yl]-2-thiophen-2-ylacetamide;

6-Chloro-N-[2-[2-[[3-(trifluoromethyl)phenyl]sulfonyl]-ethylsulfanyl]-pyridin-3-yl]-pyridine-3-carboxylic acid amide;

2-Pyridin-4-yl-N-[2-[2-[[3-(trifluoromethyl)phenyl]sulfonyl]-ethylsulfanyl]-pyridin-3-yl]acetamide;

2-(3-Hydroxyphenyl)-N-[2-[2-[[3-(trifluoromethyl)phenyl]sulfonyl]-ethylsulfanyl]-pyridin-3-yl]acetamide;

N-[2-[2-[[3-(Trifluoromethyl)phenyl]sulfonyl]-ethylsulfanyl]-pyridin-3-yl]-tetrahydropyrane-3-carboxylic acid amide;

2-Tetrahydropyran-2-yl-N-[2-[2-[[3-(trifluoromethyl)phenyl]sulfonyl]-ethylsulfanyl]-pyridin-3-yl]acetamide;

2-Tetrahydropyran-4-yl-N-[2-[2-[[3-(trifluoromethyl)phenyl]sulfonyl]-ethylsulfanyl]-pyridin-3-yl]acetamide;

3-Cyclohexyl-N-[2-[2-[[3-(trifluoromethyl)phenyl]sulfonyl]-ethylsulfanyl]-pyridin-3-yl]propionamide;

2-Cyclohexyl-N-[2-(2-phenylsulfanyl-ethylsulfanyl)-pyridin-3-yl]acetamide;

N-[2-(2-Phenoxy-ethylsulfanyl)-pyridin-3-yl]-2-thiophen-2-yl acetamide;

2-Pyridin-3-yl-N-[2-[2-[[3-(trifluoromethyl)phenyl]sulfonyl]-ethylsulfanyl]-pyridin-3-yl]acetamide;

3-Hydroxy-N-[2-[2-[[3-(trifluoromethyl)phenyl]sulfonyl]-ethylsulfanyl]-pyridin-3-yl]benzamide;

N-[2-[2-[[3-(Trifluoromethyl)phenyl]sulfonyl]-ethylsulfanyl]-pyridin-3-yl]-tetrahydropyrane-2-carboxylic acid amide;

2-Cycloheptyl-N-[2-[2-[[3-(trifluoromethyl)phenyl]sulfonyl]-ethylsulfanyl]-pyridin-3-yl]acetamide;

4-Fluoro-2-methoxy-N-[2-[2-[[3-(trifluoromethyl)phenyl]sulfonyl]-ethylsulfanyl]-pyridin-3-yl]benzamide;

4-Fluoro-2-hydroxy-N-[2-[2-[[3-(trifluoromethyl)phenyl]sulfonyl]-ethylsulfanyl]-pyridin-3-yl]benzamide;

2-(1,2,3,4-Tetrahydronaphthalen-2-yl)-N-[2-[2-[[3-(trifluoromethyl)phenyl]sulfonyl]-ethylsulfanyl]-pyridin-3-yl]acetamide;

2-Hydroxy-N-[2-[2-[[3-(trifluoromethyl)phenyl]sulfonyl]-ethylsulfanyl]-pyridin-3-yl]benzamide;

2-(3-Oxocyclohexyl)-N-[2-[2-[[3-(trifluoromethyl)phenyl]sulfonyl]-ethylsulfanyl]-pyridin-3-yl]acetamide;

N-[4-Methyl-2-[2-[[3-(trifluoromethyl)phenyl]sulfonyl]-ethylsulfanyl]-pyridin-3-yl]-2-thiophen-2-yl acetamide;

3-(1,2,3,4-Tetrahydronaphthalen-2-yl)-N-[2-[2-[[3-(trifluoromethyl)phenyl]sulfonyl]-ethylsulfanyl]-pyridin-3-yl]propionamide;

3-Cycloheptyl-N-[2-[2-[[3-(trifluoromethyl)phenyl]sulfonyl]-ethylsulfanyl]-pyridin-3-yl]propionamide;

2-(Benzo[b]thiophen-2-yl)-N-[2-[2-[[3-(trifluoromethyl)phenyl]sulfonyl]-ethylsulfanyl]-pyridin-3-yl]acetamide;

2-Pyridin-2-yl-N-[2-[2-[[3-(trifluoromethyl)phenyl]sulfonyl]-ethylsulfanyl]-pyridin-3-yl]acetamide;

N-[2-[2-[(4-Fluorophenyl)sulfanyl]-ethylsulfanyl]-pyridin-3-yl]-3,3-dimethyl butyramide;

2-(5-Bicyclo[2.2.1]heptanyl)-N-[2-[2-[[3-(trifluoromethyl)phenyl]sulfonyl]-ethylsulfanyl]-pyridin-3-yl]acetamide;

N-[2-[2-(4-Fluorophenoxy)-ethylsulfanyl]-pyridin-3-yl]-3,3-dimethyl butyramide;

3,4-Difluoro-N-[2-[2-(4-fluorophenoxy)-ethylsulfanyl]-pyridin-3-yl]benzamide;

3,4-Difluoro-N-[2-[3-(4-fluorophenyl)-propylsulfanyl]-pyridin-3-yl]benzamide;

N-[2-[3-(4-Fluorophenyl)-propylsulfanyl]-pyridin-3-yl]-3,3-dimethyl butyramide;

2-Cycloheptyl-N-[2-[2-[(4-fluorophenyl)sulfonyl]-ethylsulfanyl]-pyridin-3-yl]acetamide; and 2-Cyclohexyl-2,2-difluoro-N-[2-[2-[[3-(trifluoromethyl)phenyl]sulfonyl]-ethylsulfanyl]-pyridin-3-yl]acetamide; and physiologically compatible salts thereof.

13. A pharmaceutical composition comprising at least one substituted pyridinylamide according to claim 1, in the form of an individual stereoisomer or a mixture thereof, in the form of a free compound and/or a physiologically compatible salt thereof, and optionally one or more suitable additives and/or auxiliary substances and/or optionally further active ingredients.

14. A method of treating a disorder in a patient in need of such treatment, said disorder being at least one disorder selected from the group consisting of pain and epilepsy, said method comprising administering to said patient an amount effective to treat said disorder of at least one substituted pyridinylamide according to claim 1, each in the form of an individual stereoisomer or a mixture thereof, and in the form of a free compound and/or a physiologically compatible salt thereof.

* * * * *

UNITED STATES PATENT AND TRADEMARK OFFICE
CERTIFICATE OF CORRECTION

PATENT NO. : 8,247,573 B2  Page 1 of 1
APPLICATION NO. : 12/720836
DATED : August 21, 2012
INVENTOR(S) : Kühnert et al.

It is certified that error appears in the above-identified patent and that said Letters Patent is hereby corrected as shown below:

In the Specification

Column 1, line 44, "post" -- should read -- Dost --.

Column 7, line 54, "OF$_3$" -- should read -- CF$_3$ --.

Column 7, line 54, "ON" -- should read -- CN --.

Column 8, line 40, "C(=O)C$_{1-8}$ alkyl" -- should read -- O-C(=O)C$_{1-8}$ alkyl --.

Column 12, line 50, "OF$_3$" -- should read -- CF$_3$ --.

Column 12, line 54, "OF$_3$" -- should read -- CF$_3$ --.

Column 31, line 13, "S-30" -- should read -- 5-30 --.

In the Claims

Column 37, line 65, "4-9 N[2-[2-" -- should read -- N[2-[2- --.

Column 38, line 25, "ylacetamide" -- should read -- yl acetamide --.

Signed and Sealed this
Eleventh Day of March, 2014

Michelle K. Lee
*Deputy Director of the United States Patent and Trademark Office*